(12) United States Patent
Robaina et al.

(10) Patent No.: US 12,016,719 B2
(45) Date of Patent: Jun. 25, 2024

(54) PATIENT VIEWING SYSTEM

(71) Applicant: Magic Leap, Inc., Plantation, FL (US)

(72) Inventors: Nastasja U Robaina, Coconut Grove, FL (US); Praveen Babu JD, Plantation, FL (US); David Charles Lundmark, Los Altos, CA (US); Alexander Ilic, Zurich (CH)

(73) Assignee: Magic Leap, Inc., Plantation, FL (US)

( * ) Notice: Subject to any disclaimer, the term of this patent is extended or adjusted under 35 U.S.C. 154(b) by 648 days.

(21) Appl. No.: 17/268,376

(22) PCT Filed: Aug. 22, 2019

(86) PCT No.: PCT/US2019/047746
§ 371 (c)(1),
(2) Date: Feb. 12, 2021

(87) PCT Pub. No.: WO2020/041615
PCT Pub. Date: Feb. 27, 2020

(65) Prior Publication Data
US 2021/0177370 A1 Jun. 17, 2021

Related U.S. Application Data

(60) Provisional application No. 62/721,516, filed on Aug. 22, 2018, provisional application No. 62/771,534, filed on Nov. 26, 2018.

(51) Int. Cl.
*A61B 6/00* (2006.01)
*A61B 5/06* (2006.01)
(Continued)

(52) U.S. Cl.
CPC .............. *A61B 6/547* (2013.01); *A61B 5/06* (2013.01); *A61B 5/065* (2013.01); *A61B 5/066* (2013.01);
(Continued)

(58) Field of Classification Search
None
See application file for complete search history.

(56) References Cited

U.S. PATENT DOCUMENTS

| 4,344,092 A | 8/1982 | Miller |
| 4,652,930 A | 3/1987 | Crawford |

(Continued)

FOREIGN PATENT DOCUMENTS

| CN | 100416340 C | * 9/2008 | ......... G02B 27/0081 |
| CN | 101449270 A | 6/2009 | |

(Continued)

OTHER PUBLICATIONS

Communication Pursuant to Article 94(3) EPC dated Jan. 4, 2022, European Patent Application No. 20154070.5, (8 pages).

(Continued)

*Primary Examiner* — Mohammed Rachedine
(74) *Attorney, Agent, or Firm* — Stephen M. De Klerk

(57) ABSTRACT

A method of viewing a patient including inserting a catheter is described for health procedure navigation. A CT scan is carried out on a body part of a patient. Raw data from the CT scan is processed to create three-dimensional image data, storing the image data in the data store. Projectors receive generated light in a pattern representative of the image data and waveguides guide the light to a retina of an eye of a viewer while light from an external surface of the body transmits to the retina of the eye so that the viewer sees the external surface of the body augmented with the processed data rendering of the body part.

24 Claims, 12 Drawing Sheets

(51) Int. Cl.
  *A61B 6/02*    (2006.01)
  *A61B 6/03*    (2006.01)
  *A61B 6/46*    (2024.01)
  *G06T 7/00*    (2017.01)
  *G06T 15/00*   (2011.01)
  *H04N 13/275*  (2018.01)
  *H04N 13/344*  (2018.01)

(52) U.S. Cl.
  CPC .............. *A61B 6/022* (2013.01); *A61B 6/032* (2013.01); *A61B 6/464* (2013.01); *A61B 6/466* (2013.01); *A61B 6/5205* (2013.01); *G06T 7/0012* (2013.01); *G06T 15/00* (2013.01); *A61B 2560/066* (2013.01); *A61B 2562/0219* (2013.01)

(56) References Cited

U.S. PATENT DOCUMENTS

| | | |
|---|---|---|
| 4,810,080 A | 3/1989 | Grendol et al. |
| 4,997,268 A | 3/1991 | Dauvergne |
| 5,007,727 A | 4/1991 | Kahaney et al. |
| 5,074,295 A | 12/1991 | Willis |
| 5,240,220 A | 8/1993 | Elberbaum |
| 5,251,635 A | 10/1993 | Dumoulin et al. |
| 5,410,763 A | 5/1995 | Bolle |
| 5,455,625 A | 10/1995 | Englander |
| 5,495,286 A | 2/1996 | Adair |
| 5,497,463 A | 3/1996 | Stein et al. |
| 5,659,701 A | 8/1997 | Amit et al. |
| 5,682,255 A | 10/1997 | Friesem et al. |
| 5,689,669 A | 11/1997 | Lynch |
| 5,826,092 A | 10/1998 | Flannery |
| 5,854,872 A | 12/1998 | Tai |
| 5,864,365 A | 1/1999 | Sramek et al. |
| 5,937,202 A | 8/1999 | Crosetto |
| 6,002,853 A | 12/1999 | De Hond |
| 6,012,811 A | 1/2000 | Chao et al. |
| 6,016,160 A | 1/2000 | Coombs et al. |
| 6,064,749 A | 5/2000 | Hirota et al. |
| 6,076,927 A | 6/2000 | Owens |
| 6,079,982 A | 6/2000 | Meader |
| 6,117,923 A | 9/2000 | Amagai et al. |
| 6,119,147 A | 9/2000 | Toomey et al. |
| 6,124,977 A | 9/2000 | Takahashi |
| 6,179,619 B1 | 1/2001 | Tanaka |
| 6,191,809 B1 | 2/2001 | Hori et al. |
| 6,219,045 B1 | 4/2001 | Leahy et al. |
| 6,243,091 B1 | 6/2001 | Berstis |
| 6,271,843 B1 | 8/2001 | Lection et al. |
| 6,362,817 B1 | 3/2002 | Powers et al. |
| 6,375,369 B1 | 4/2002 | Schneider et al. |
| 6,385,735 B1 | 5/2002 | Wilson |
| 6,396,522 B1 | 5/2002 | Vu |
| 6,414,679 B1 | 7/2002 | Miodonski et al. |
| 6,538,655 B1 | 3/2003 | Kubota |
| 6,541,736 B1 | 4/2003 | Huang et al. |
| 6,570,563 B1 | 5/2003 | Honda |
| 6,573,903 B2 | 6/2003 | Gantt |
| 6,590,593 B1 | 7/2003 | Robertson et al. |
| 6,621,508 B1 | 9/2003 | Shiraishi et al. |
| 6,690,393 B2 | 2/2004 | Heron et al. |
| 6,757,068 B2 | 6/2004 | Foxlin |
| 6,784,901 B1 | 8/2004 | Harvfey et al. |
| 6,961,055 B2 | 11/2005 | Doak |
| 7,046,515 B1 | 5/2006 | Wyatt |
| 7,051,219 B2 | 5/2006 | Hwang |
| 7,076,674 B2 | 7/2006 | Cervantes |
| 7,111,290 B1 | 9/2006 | Yates, Jr. |
| 7,119,819 B1 | 10/2006 | Robertson et al. |
| 7,219,245 B1 | 5/2007 | Raghuvanshi |
| 7,382,288 B1 | 6/2008 | Wilson |
| 7,414,629 B2 | 8/2008 | Santodomingo |
| 7,431,453 B2 | 10/2008 | Hogan |
| 7,467,356 B2 | 12/2008 | Gettman et al. |
| 7,542,040 B2 | 6/2009 | Templeman |
| 7,573,640 B2 | 8/2009 | Nivon et al. |
| 7,653,877 B2 | 1/2010 | Matsuda |
| 7,663,625 B2 | 2/2010 | Chartier et al. |
| 7,724,980 B1 | 5/2010 | Shenzhi |
| 7,746,343 B1 | 6/2010 | Charaniya et al. |
| 7,751,662 B2 | 7/2010 | Kleemann |
| 7,758,185 B2 | 7/2010 | Lewis |
| 7,788,323 B2 | 8/2010 | Greenstein et al. |
| 7,804,507 B2 | 9/2010 | Yang et al. |
| 7,814,429 B2 | 10/2010 | Buffet et al. |
| 7,817,150 B2 | 10/2010 | Reichard et al. |
| 7,844,724 B2 | 11/2010 | Van Wie et al. |
| 8,060,759 B1 | 11/2011 | Arnan et al. |
| 8,120,851 B2 | 2/2012 | Iwasa |
| 8,214,660 B2 | 7/2012 | Capps, Jr. |
| 8,246,408 B2 | 8/2012 | Elliot |
| 8,353,594 B2 | 1/2013 | Lewis |
| 8,360,578 B2 | 1/2013 | Nummela et al. |
| 8,508,676 B2 | 8/2013 | Silverstein et al. |
| 8,547,638 B2 | 10/2013 | Levola |
| 8,605,764 B1 | 10/2013 | Rothaar et al. |
| 8,619,365 B2 | 12/2013 | Harris et al. |
| 8,696,113 B2 | 4/2014 | Lewis |
| 8,698,701 B2 | 4/2014 | Margulis |
| 8,733,927 B1 | 5/2014 | Lewis |
| 8,736,636 B2 | 5/2014 | Kang |
| 8,759,929 B2 | 6/2014 | Shiozawa et al. |
| 8,793,770 B2 | 7/2014 | Lim |
| 8,823,855 B2 | 9/2014 | Hwang |
| 8,847,988 B2 | 9/2014 | Geisner et al. |
| 8,874,673 B2 | 10/2014 | Kim |
| 9,010,929 B2 | 4/2015 | Lewis |
| 9,015,501 B2 | 4/2015 | Gee |
| 9,086,537 B2 | 7/2015 | Iwasa et al. |
| 9,095,437 B2 | 8/2015 | Boyden et al. |
| 9,239,473 B2 | 1/2016 | Lewis |
| 9,244,293 B2 | 1/2016 | Lewis |
| 9,244,533 B2 | 1/2016 | Friend et al. |
| 9,383,823 B2 | 7/2016 | Geisner et al. |
| 9,489,027 B1 | 11/2016 | Ogletree |
| 9,519,305 B2 | 12/2016 | Wolfe |
| 9,581,820 B2 | 2/2017 | Robbins |
| 9,582,060 B2 | 2/2017 | Balatsos |
| 9,658,473 B2 | 5/2017 | Lewis |
| 9,671,566 B2 | 6/2017 | Abovitz et al. |
| 9,671,615 B1 | 6/2017 | Vallius et al. |
| 9,696,795 B2 | 7/2017 | Marcolina et al. |
| 9,798,144 B2 | 10/2017 | Sako et al. |
| 9,874,664 B2 | 1/2018 | Stevens et al. |
| 9,880,441 B1 | 1/2018 | Osterhout |
| 9,918,058 B2 | 3/2018 | Takahasi et al. |
| 9,955,862 B2 | 5/2018 | Freeman et al. |
| 9,978,118 B1 | 5/2018 | Ozgumer et al. |
| 9,996,797 B1 | 6/2018 | Holz et al. |
| 10,018,844 B2 | 7/2018 | Levola et al. |
| 10,082,865 B1 | 9/2018 | Raynal et al. |
| 10,151,937 B2 | 12/2018 | Lewis |
| 10,185,147 B2 | 1/2019 | Lewis |
| 10,218,679 B1 | 2/2019 | Jawahar |
| 10,241,545 B1 | 3/2019 | Richards et al. |
| 10,317,680 B1 | 6/2019 | Richards et al. |
| 10,436,594 B2 | 10/2019 | Belt et al. |
| 10,516,853 B1 | 12/2019 | Gibson et al. |
| 10,551,879 B1 | 2/2020 | Richards et al. |
| 10,578,870 B2 | 3/2020 | Kimmel |
| 10,698,202 B2 | 6/2020 | Kimmel et al. |
| 10,856,107 B2 | 10/2020 | Mycek et al. |
| 10,825,424 B2 | 11/2020 | Zhang |
| 10,987,176 B2 | 4/2021 | Poltaretskyi et al. |
| 11,190,681 B1 | 11/2021 | Brook et al. |
| 11,209,656 B1 | 12/2021 | Choi et al. |
| 11,236,993 B1 | 2/2022 | Hall et al. |
| 2001/0010598 A1 | 8/2001 | Aritake et al. |
| 2001/0018667 A1 | 8/2001 | Kim |
| 2002/0007463 A1 | 1/2002 | Fung |
| 2002/0108064 A1 | 2/2002 | Nunally |
| 2002/0063913 A1 | 5/2002 | Nakamura et al. |
| 2002/0071050 A1 | 6/2002 | Homberg |

(56) References Cited

U.S. PATENT DOCUMENTS

| | | |
|---|---|---|
| 2002/0095463 A1 | 7/2002 | Matsuda |
| 2002/0113820 A1 | 8/2002 | Robinson et al. |
| 2002/0122648 A1 | 9/2002 | Mule' et al. |
| 2002/0140848 A1 | 10/2002 | Cooper et al. |
| 2003/0028816 A1 | 2/2003 | Bacon |
| 2003/0048456 A1 | 3/2003 | Hill |
| 2003/0067685 A1 | 4/2003 | Niv |
| 2003/0077458 A1 | 4/2003 | Korenaga et al. |
| 2003/0080976 A1 | 5/2003 | Satoh et al. |
| 2003/0115494 A1 | 6/2003 | Cervantes |
| 2003/0218614 A1 | 11/2003 | Lavelle et al. |
| 2003/0219992 A1 | 11/2003 | Schaper |
| 2003/0226047 A1 | 12/2003 | Park |
| 2004/0001533 A1 | 1/2004 | Tran et al. |
| 2004/0021600 A1 | 2/2004 | Wittenberg |
| 2004/0025069 A1 | 2/2004 | Gary et al. |
| 2004/0042377 A1 | 3/2004 | Nikoloai et al. |
| 2004/0073822 A1 | 4/2004 | Greco |
| 2004/0073825 A1 | 4/2004 | Itoh |
| 2004/0111248 A1 | 6/2004 | Granny et al. |
| 2004/0113887 A1 | 6/2004 | Pair et al. |
| 2004/0174496 A1 | 9/2004 | Ji et al. |
| 2004/0186902 A1 | 9/2004 | Stewart |
| 2004/0193441 A1 | 9/2004 | Altieri |
| 2004/0201857 A1 | 10/2004 | Foxlin |
| 2004/0238732 A1 | 12/2004 | State et al. |
| 2004/0240072 A1 | 12/2004 | Schindler et al. |
| 2004/0246391 A1 | 12/2004 | Travis |
| 2004/0268159 A1 | 12/2004 | Aasheim et al. |
| 2005/0001977 A1 | 1/2005 | Zelman |
| 2005/0034002 A1 | 2/2005 | Flautner |
| 2005/0093719 A1 | 5/2005 | Okamoto et al. |
| 2005/0128212 A1 | 6/2005 | Edecker et al. |
| 2005/0157159 A1 | 7/2005 | Komiya et al. |
| 2005/0177385 A1 | 8/2005 | Hull |
| 2005/0231599 A1 | 10/2005 | Yamasaki |
| 2005/0273792 A1 | 12/2005 | Inohara et al. |
| 2006/0013435 A1 | 1/2006 | Rhoads |
| 2006/0015821 A1 | 1/2006 | Jacques Parker et al. |
| 2006/0019723 A1 | 1/2006 | Vorenkamp |
| 2006/0038880 A1 | 2/2006 | Starkweather et al. |
| 2006/0050224 A1 | 3/2006 | Smith |
| 2006/0090092 A1 | 4/2006 | Verhulst |
| 2006/0126181 A1 | 6/2006 | Levola |
| 2006/0129852 A1 | 6/2006 | Bonola |
| 2006/0132914 A1 | 6/2006 | Weiss et al. |
| 2006/0179329 A1 | 8/2006 | Terechko |
| 2006/0221448 A1 | 10/2006 | Nivon et al. |
| 2006/0228073 A1 | 10/2006 | Mukawa et al. |
| 2006/0250322 A1 | 11/2006 | Hall et al. |
| 2006/0259621 A1 | 11/2006 | Ranganathan |
| 2006/0268220 A1 | 11/2006 | Hogan |
| 2007/0058248 A1 | 3/2007 | Nguyen et al. |
| 2007/0103836 A1 | 5/2007 | Oh |
| 2007/0124730 A1 | 5/2007 | Pytel |
| 2007/0159673 A1 | 7/2007 | Freeman et al. |
| 2007/0188837 A1 | 8/2007 | Shimizu et al. |
| 2007/0198886 A1 | 8/2007 | Saito |
| 2007/0204672 A1 | 9/2007 | Huang et al. |
| 2007/0213952 A1 | 9/2007 | Cirelli |
| 2007/0283247 A1 | 12/2007 | Brenneman et al. |
| 2008/0002259 A1 | 1/2008 | Ishizawa et al. |
| 2008/0002260 A1 | 1/2008 | Arrouy et al. |
| 2008/0030429 A1 | 2/2008 | Hailpern |
| 2008/0043334 A1 | 2/2008 | Itzkovitch et al. |
| 2008/0046773 A1 | 2/2008 | Ham |
| 2008/0063802 A1 | 3/2008 | Maula et al. |
| 2008/0068557 A1 | 3/2008 | Menduni et al. |
| 2008/0125218 A1 | 5/2008 | Collins |
| 2008/0146942 A1* | 6/2008 | Dala-Krishna ...... A61B 8/4488 600/466 |
| 2008/0173036 A1 | 7/2008 | Willaims |
| 2008/0177506 A1 | 7/2008 | Kim |
| 2008/0183190 A1 | 7/2008 | Adcox et al. |
| 2008/0205838 A1 | 8/2008 | Crippa et al. |
| 2008/0215907 A1 | 9/2008 | Wilson |
| 2008/0225393 A1 | 9/2008 | Rinko |
| 2008/0235570 A1 | 9/2008 | Sawada et al. |
| 2008/0246693 A1 | 10/2008 | Hailpern et al. |
| 2008/0316768 A1 | 12/2008 | Travis |
| 2009/0076791 A1 | 3/2009 | Rhoades et al. |
| 2009/0091583 A1 | 4/2009 | McCoy |
| 2009/0153797 A1 | 6/2009 | Allon et al. |
| 2009/0224416 A1 | 9/2009 | Laakkonen et al. |
| 2009/0245730 A1 | 10/2009 | Kleemann |
| 2009/0287728 A1 | 11/2009 | Martine et al. |
| 2009/0300528 A1 | 12/2009 | Stambaugh |
| 2009/0310633 A1 | 12/2009 | Ikegami |
| 2010/0005326 A1 | 1/2010 | Archer |
| 2010/0019962 A1 | 1/2010 | Fujita |
| 2010/0056274 A1 | 3/2010 | Uusitalo et al. |
| 2010/0063854 A1 | 3/2010 | Purvis et al. |
| 2010/0070378 A1 | 3/2010 | Trotman et al. |
| 2010/0079841 A1 | 4/2010 | Levola |
| 2010/0115428 A1 | 5/2010 | Shuping et al. |
| 2010/0153934 A1 | 6/2010 | Lachner |
| 2010/0194632 A1 | 8/2010 | Raento et al. |
| 2010/0205541 A1 | 8/2010 | Rappaport et al. |
| 2010/0214284 A1 | 8/2010 | Rieffel et al. |
| 2010/0232016 A1 | 9/2010 | Landa et al. |
| 2010/0232031 A1 | 9/2010 | Batchko et al. |
| 2010/0244168 A1 | 9/2010 | Shiozawa et al. |
| 2010/0274567 A1 | 10/2010 | Carlson et al. |
| 2010/0274627 A1 | 10/2010 | Carlson |
| 2010/0277803 A1 | 11/2010 | Pockett et al. |
| 2010/0284085 A1 | 11/2010 | Laakkonen |
| 2010/0287485 A1 | 11/2010 | Bertolami et al. |
| 2010/0296163 A1 | 11/2010 | Sarikko |
| 2010/0309687 A1 | 12/2010 | Sampsell et al. |
| 2011/0010636 A1 | 1/2011 | Hamilton, II et al. |
| 2011/0021263 A1 | 1/2011 | Anderson et al. |
| 2011/0022870 A1 | 1/2011 | Mcgrane |
| 2011/0041083 A1 | 2/2011 | Gabai et al. |
| 2011/0050640 A1 | 3/2011 | Lundback et al. |
| 2011/0050655 A1 | 3/2011 | Mukawa |
| 2011/0064268 A1 | 3/2011 | Cobb et al. |
| 2011/0122240 A1 | 5/2011 | Becker |
| 2011/0145617 A1 | 6/2011 | Thomson et al. |
| 2011/0170801 A1 | 7/2011 | Lu et al. |
| 2011/0218733 A1 | 9/2011 | Hamza et al. |
| 2011/0286735 A1 | 11/2011 | Temblay |
| 2011/0291969 A1 | 12/2011 | Rashid et al. |
| 2012/0011389 A1 | 1/2012 | Driesen |
| 2012/0050535 A1 | 3/2012 | Densham et al. |
| 2012/0075501 A1 | 3/2012 | Oyagi et al. |
| 2012/0081392 A1 | 4/2012 | Arthur |
| 2012/0089854 A1 | 4/2012 | Breakstone |
| 2012/0113235 A1 | 5/2012 | Shintani |
| 2012/0127062 A1 | 5/2012 | Bar-Zeev et al. |
| 2012/0154557 A1 | 6/2012 | Perez et al. |
| 2012/0215094 A1* | 8/2012 | Rahimian ............ A61B 6/503 600/414 |
| 2012/0218301 A1 | 8/2012 | Miller |
| 2012/0246506 A1 | 9/2012 | Knight |
| 2012/0249416 A1 | 10/2012 | Maciocci et al. |
| 2012/0249741 A1 | 10/2012 | Maciocci et al. |
| 2012/0260083 A1 | 10/2012 | Andrews |
| 2012/0307075 A1 | 12/2012 | Margalitq |
| 2012/0307362 A1 | 12/2012 | Silverstein et al. |
| 2012/0320460 A1 | 12/2012 | Levola |
| 2012/0326948 A1 | 12/2012 | Crocco et al. |
| 2013/0021486 A1 | 1/2013 | Richardon |
| 2013/0050642 A1 | 2/2013 | Lewis et al. |
| 2013/0050833 A1 | 2/2013 | Lewis et al. |
| 2013/0051730 A1 | 2/2013 | Travers et al. |
| 2013/0502058 | 2/2013 | Liu et al. |
| 2013/0061240 A1 | 3/2013 | Yan et al. |
| 2013/0077049 A1 | 3/2013 | Bohn |
| 2013/0077170 A1 | 3/2013 | Ukuda |
| 2013/0094148 A1 | 4/2013 | Sloane |
| 2013/0129282 A1 | 5/2013 | Li |
| 2013/0162940 A1 | 6/2013 | Kurtin et al. |
| 2013/0169923 A1 | 7/2013 | Schnoll et al. |
| 2013/0205126 A1 | 8/2013 | Kruglick |

(56) References Cited

U.S. PATENT DOCUMENTS

| | | |
|---|---|---|
| 2013/0222386 A1 | 8/2013 | Tannhauser et al. |
| 2013/0268257 A1 | 10/2013 | Hu |
| 2013/0278633 A1 | 10/2013 | Ahn et al. |
| 2013/0314789 A1 | 11/2013 | Saarikko et al. |
| 2013/0318276 A1 | 11/2013 | Dalal |
| 2013/0336138 A1 | 12/2013 | Venkatraman et al. |
| 2013/0342564 A1 | 12/2013 | Kinnebrew et al. |
| 2013/0342570 A1 | 12/2013 | Kinnebrew et al. |
| 2013/0342571 A1 | 12/2013 | Kinnebrew et al. |
| 2013/0343408 A1 | 12/2013 | Cook |
| 2014/0002329 A1 | 1/2014 | Nishimaki et al. |
| 2014/0013098 A1 | 1/2014 | Yeung |
| 2014/0016821 A1 | 1/2014 | Arth et al. |
| 2014/0022819 A1 | 1/2014 | Oh et al. |
| 2014/0078023 A1 | 3/2014 | Ikeda et al. |
| 2014/0082526 A1 | 3/2014 | Park et al. |
| 2014/0119598 A1 | 5/2014 | Ramachandran et al. |
| 2014/0126769 A1 | 5/2014 | Reitmayr et al. |
| 2014/0140653 A1 | 5/2014 | Brown et al. |
| 2014/0149573 A1 | 5/2014 | Tofighbakhsh et al. |
| 2014/0168260 A1 | 6/2014 | O'Brien et al. |
| 2014/0244983 A1 | 8/2014 | McDonald et al. |
| 2014/0266987 A1 | 9/2014 | Magyari |
| 2014/0267419 A1 | 9/2014 | Ballard et al. |
| 2014/0274391 A1 | 9/2014 | Stafford |
| 2014/0282105 A1 | 9/2014 | Nordstrom |
| 2014/0292645 A1 | 10/2014 | Tsurumi et al. |
| 2014/0313228 A1 | 10/2014 | Kasahara |
| 2014/0340449 A1 | 11/2014 | Plagemann et al. |
| 2014/0359589 A1 | 12/2014 | Kodsky et al. |
| 2014/0375680 A1 | 12/2014 | Ackerman et al. |
| 2015/0005785 A1 | 1/2015 | Olson |
| 2015/0009099 A1 | 1/2015 | Queen |
| 2015/0077312 A1 | 3/2015 | Wang |
| 2015/0097719 A1 | 4/2015 | Balachandreswaran et al. |
| 2015/0123966 A1 | 5/2015 | Newman |
| 2015/0130790 A1 | 5/2015 | Vazquez, II et al. |
| 2015/0134995 A1 | 5/2015 | Park et al. |
| 2015/0138248 A1 | 5/2015 | Schrader |
| 2015/0155939 A1 | 6/2015 | Oshima et al. |
| 2015/0168221 A1 | 6/2015 | Mao et al. |
| 2015/0205126 A1 | 7/2015 | Schowengerdt |
| 2015/0235427 A1 | 8/2015 | Nobori et al. |
| 2015/0235431 A1 | 8/2015 | Schowengerdt |
| 2015/0253651 A1 | 9/2015 | Russell et al. |
| 2015/0256484 A1 | 9/2015 | Cameron |
| 2015/0269784 A1 | 9/2015 | Miyawaki et al. |
| 2015/0294483 A1 | 10/2015 | Wells et al. |
| 2015/0301955 A1 | 10/2015 | Yakovenko et al. |
| 2015/0310657 A1 | 10/2015 | Eden |
| 2015/0338915 A1 | 11/2015 | Publicover et al. |
| 2015/0355481 A1 | 12/2015 | Hilkes et al. |
| 2016/0004102 A1 | 1/2016 | Nisper et al. |
| 2016/0015470 A1 | 1/2016 | Border |
| 2016/0027215 A1 | 1/2016 | Burns et al. |
| 2016/0033770 A1 | 2/2016 | Fujimaki et al. |
| 2016/0051217 A1* | 2/2016 | Douglas ............... A61B 6/481 345/419 |
| 2016/0077338 A1 | 3/2016 | Robbins et al. |
| 2016/0085285 A1 | 3/2016 | Mangione-Smith |
| 2016/0085300 A1 | 3/2016 | Robbins et al. |
| 2016/0091720 A1 | 3/2016 | Stafford et al. |
| 2016/0093099 A1 | 3/2016 | Bridges |
| 2016/0093269 A1 | 3/2016 | Buckley et al. |
| 2016/0103326 A1* | 4/2016 | Kimura ............... G02B 27/0179 345/690 |
| 2016/0123745 A1 | 5/2016 | Cotier et al. |
| 2016/0139402 A1 | 5/2016 | Lapstun |
| 2016/0139411 A1 | 5/2016 | Kang et al. |
| 2016/0155273 A1 | 6/2016 | Lyren et al. |
| 2016/0180596 A1 | 6/2016 | Gonzalez del Rosario |
| 2016/0187654 A1 | 6/2016 | Border et al. |
| 2016/0191887 A1 | 6/2016 | Casas |
| 2016/0202496 A1 | 7/2016 | Billetz et al. |
| 2016/0217624 A1 | 7/2016 | Finn et al. |
| 2016/0266412 A1 | 9/2016 | Yoshida |
| 2016/0267708 A1 | 9/2016 | Nistico et al. |
| 2016/0274733 A1 | 9/2016 | Hasegawa et al. |
| 2016/0287337 A1 | 10/2016 | Aram et al. |
| 2016/0300388 A1 | 10/2016 | Stafford et al. |
| 2016/0321551 A1 | 11/2016 | Priness et al. |
| 2016/0327798 A1 | 11/2016 | Xiao et al. |
| 2016/0334279 A1 | 11/2016 | Mittleman et al. |
| 2016/0357255 A1 | 12/2016 | Lindh et al. |
| 2016/0370404 A1 | 12/2016 | Quadrat et al. |
| 2016/0370510 A1 | 12/2016 | Thomas |
| 2017/0038607 A1 | 2/2017 | Camara |
| 2017/0060225 A1 | 3/2017 | Zha et al. |
| 2017/0061696 A1 | 3/2017 | Li et al. |
| 2017/0064066 A1 | 3/2017 | Das et al. |
| 2017/0100664 A1 | 4/2017 | Osterhout et al. |
| 2017/0102544 A1 | 4/2017 | Vallius et al. |
| 2017/0115487 A1 | 4/2017 | Travis |
| 2017/0122725 A1 | 5/2017 | Yeoh et al. |
| 2017/0123526 A1 | 5/2017 | Trail et al. |
| 2017/0127295 A1 | 5/2017 | Black et al. |
| 2017/0131569 A1 | 5/2017 | Aschwanden et al. |
| 2017/0147066 A1 | 5/2017 | Katz et al. |
| 2017/0160518 A1 | 6/2017 | Lanman et al. |
| 2017/0161951 A1 | 6/2017 | Fix et al. |
| 2017/0185261 A1 | 6/2017 | Perez et al. |
| 2017/0192239 A1 | 7/2017 | Nakamura et al. |
| 2017/0201709 A1 | 7/2017 | Igarashi et al. |
| 2017/0205903 A1 | 7/2017 | Miller et al. |
| 2017/0206668 A1 | 7/2017 | Poulos et al. |
| 2017/0213388 A1 | 7/2017 | Margolis et al. |
| 2017/0214907 A1 | 7/2017 | Lapstun |
| 2017/0219841 A1 | 8/2017 | Popovich et al. |
| 2017/0232345 A1 | 8/2017 | Rofougaran et al. |
| 2017/0235126 A1 | 8/2017 | DiDomenico |
| 2017/0235129 A1 | 8/2017 | Kamakura |
| 2017/0235142 A1 | 8/2017 | Wall et al. |
| 2017/0235144 A1 | 8/2017 | Piskunov et al. |
| 2017/0235147 A1 | 8/2017 | Kamakura |
| 2017/0243403 A1 | 8/2017 | Daniels et al. |
| 2017/0246070 A1 | 8/2017 | Osterhout et al. |
| 2017/0254832 A1 | 9/2017 | Ho et al. |
| 2017/0256096 A1 | 9/2017 | Faaborg et al. |
| 2017/0258526 A1 | 9/2017 | Lang |
| 2017/0266529 A1 | 9/2017 | Reikmoto |
| 2017/0270712 A1 | 9/2017 | Tyson et al. |
| 2017/0281054 A1 | 10/2017 | Stever et al. |
| 2017/0287376 A1 | 10/2017 | Bakar et al. |
| 2017/0293141 A1 | 10/2017 | Schowengerdt et al. |
| 2017/0307886 A1 | 10/2017 | Stenberg et al. |
| 2017/0307891 A1 | 10/2017 | Bucknor et al. |
| 2017/0312032 A1 | 11/2017 | Amanatullah et al. |
| 2017/0322418 A1 | 11/2017 | Liu et al. |
| 2017/0322426 A1 | 11/2017 | Tervo |
| 2017/0329137 A1 | 11/2017 | Tervo |
| 2017/0332098 A1 | 11/2017 | Rusanovskyy et al. |
| 2017/0336636 A1 | 11/2017 | Amitai et al. |
| 2017/0357332 A1 | 12/2017 | Balan et al. |
| 2017/0363871 A1 | 12/2017 | Vallius |
| 2017/0371394 A1 | 12/2017 | Chan |
| 2017/0371661 A1 | 12/2017 | Sparling |
| 2018/0014266 A1 | 1/2018 | Chen |
| 2018/0024289 A1 | 1/2018 | Fattal |
| 2018/0044173 A1 | 2/2018 | Netzer |
| 2018/0052007 A1 | 2/2018 | Teskey et al. |
| 2018/0052501 A1 | 2/2018 | Jones, Jr. et al. |
| 2018/0059305 A1 | 3/2018 | Popovich et al. |
| 2018/0067779 A1 | 3/2018 | Pillalamarri et al. |
| 2018/0070855 A1 | 3/2018 | Eichler |
| 2018/0082480 A1 | 3/2018 | White et al. |
| 2018/0084245 A1 | 3/2018 | Lapstun |
| 2018/0088185 A1 | 3/2018 | Woods et al. |
| 2018/0102981 A1 | 4/2018 | Kurtzman et al. |
| 2018/0108179 A1 | 4/2018 | Tomlin et al. |
| 2018/0114298 A1 | 4/2018 | Malaika et al. |
| 2018/0129112 A1 | 5/2018 | Osterhout |
| 2018/0131907 A1 | 5/2018 | Schmirler et al. |
| 2018/0136466 A1 | 5/2018 | Ko |
| 2018/0144691 A1 | 5/2018 | Choi et al. |

(56) References Cited

U.S. PATENT DOCUMENTS

| | | |
|---|---|---|
| 2018/0150971 A1 | 5/2018 | Adachi et al. |
| 2018/0151796 A1 | 5/2018 | Akahane |
| 2018/0172995 A1 | 6/2018 | Lee et al. |
| 2018/0188115 A1 | 7/2018 | Hsu et al. |
| 2018/0189568 A1 | 7/2018 | Powderly et al. |
| 2018/0190017 A1 | 7/2018 | Mendez et al. |
| 2018/0191990 A1 | 7/2018 | Motoyama et al. |
| 2018/0217395 A1 | 8/2018 | Lin et al. |
| 2018/0218545 A1 | 8/2018 | Garcia et al. |
| 2018/0250589 A1 | 9/2018 | Cossairt et al. |
| 2018/0260218 A1 | 9/2018 | Gopal |
| 2018/0284877 A1 | 10/2018 | Klein |
| 2018/0292654 A1 | 10/2018 | Wall et al. |
| 2018/0299678 A1 | 10/2018 | Singer et al. |
| 2018/0357472 A1 | 12/2018 | Dreessen |
| 2019/0011691 A1 | 1/2019 | Peyman |
| 2019/0056591 A1 | 2/2019 | Tervo et al. |
| 2019/0087015 A1 | 3/2019 | Lam et al. |
| 2019/0101758 A1 | 4/2019 | Zhu et al. |
| 2019/0107723 A1 | 4/2019 | Lee et al. |
| 2019/0137788 A1 | 5/2019 | Suen |
| 2019/0155034 A1 | 5/2019 | Singer et al. |
| 2019/0155439 A1 | 5/2019 | Mukherjee et al. |
| 2019/0158926 A1 | 5/2019 | Kang et al. |
| 2019/0162950 A1 | 5/2019 | Lapstun |
| 2019/0167095 A1 | 6/2019 | Krueger |
| 2019/0172216 A1 | 6/2019 | Ninan et al. |
| 2019/0178654 A1 | 6/2019 | Hare |
| 2019/0182415 A1 | 6/2019 | Sivan |
| 2019/0196690 A1 | 6/2019 | Chong et al. |
| 2019/0206116 A1 | 7/2019 | Xu et al. |
| 2019/0219815 A1 | 7/2019 | Price et al. |
| 2019/0243123 A1 | 8/2019 | Bohn |
| 2019/0287270 A1 | 9/2019 | Nakamura et al. |
| 2019/0318502 A1 | 10/2019 | He et al. |
| 2019/0318540 A1 | 10/2019 | Piemonte et al. |
| 2019/0321728 A1 | 10/2019 | Imai et al. |
| 2019/0347853 A1 | 11/2019 | Chen et al. |
| 2019/0380792 A1 | 12/2019 | Poltaretskyi et al. |
| 2019/0388182 A1 | 12/2019 | Kumar et al. |
| 2020/0066045 A1 | 2/2020 | Stahl et al. |
| 2020/0098188 A1 | 3/2020 | Bar-Zeev et al. |
| 2020/0100057 A1 | 3/2020 | Galon et al. |
| 2020/0110928 A1 | 4/2020 | Al Jazaery et al. |
| 2020/0117267 A1 | 4/2020 | Gibson et al. |
| 2020/0117270 A1 | 4/2020 | Gibson et al. |
| 2020/0184217 A1 | 6/2020 | Faulkner |
| 2020/0184653 A1 | 6/2020 | Faulker |
| 2020/0202759 A1 | 6/2020 | Ukai et al. |
| 2020/0242848 A1 | 7/2020 | Ambler et al. |
| 2020/0309944 A1 | 10/2020 | Thoresen et al. |
| 2020/0356161 A1 | 11/2020 | Wagner |
| 2020/0368616 A1 | 11/2020 | Delamont |
| 2020/0391115 A1 | 12/2020 | Leeper et al. |
| 2020/0409528 A1 | 12/2020 | Lee |
| 2021/0008413 A1 | 1/2021 | Asikainen et al. |
| 2021/0033871 A1 | 2/2021 | Jacoby et al. |
| 2021/0041951 A1 | 2/2021 | Gibson et al. |
| 2021/0053820 A1 | 2/2021 | Gurin et al. |
| 2021/0093391 A1 | 4/2021 | Poltaretskyi et al. |
| 2021/0093410 A1 | 4/2021 | Gaborit et al. |
| 2021/0093414 A1 | 4/2021 | Moore et al. |
| 2021/0097886 A1 | 4/2021 | Kuester et al. |
| 2021/0124901 A1 | 4/2021 | Liu et al. |
| 2021/0132380 A1 | 5/2021 | Wieczorek |
| 2021/0141225 A1* | 5/2021 | Meynen ............ G02B 27/0172 |
| 2021/0142582 A1 | 5/2021 | Jones et al. |
| 2021/0158023 A1 | 5/2021 | Fu et al. |
| 2021/0158627 A1 | 5/2021 | Cossairt et al. |
| 2021/0173480 A1 | 6/2021 | Osterhout et al. |
| 2022/0366598 A1 | 11/2022 | Azimi et al. |

FOREIGN PATENT DOCUMENTS

| | | | |
|---|---|---|---|
| CN | 103460255 A | 12/2013 | |
| CN | 104040410 A | 9/2014 | |
| CN | 104603675 A | 5/2015 | |
| CN | 105938426 A | 9/2016 | |
| CN | 106662754 A | 5/2017 | |
| CN | 107683497 A1 | 2/2018 | |
| CN | 109223121 A * | 1/2019 | |
| CN | 105190427 B | 11/2019 | |
| EP | 0504930 A1 | 3/1992 | |
| EP | 0535402 A1 | 4/1993 | |
| EP | 0632360 A1 | 1/1995 | |
| EP | 1215522 A2 | 6/2002 | |
| EP | 1494110 A2 | 1/2005 | |
| EP | 1938141 A1 | 7/2008 | |
| EP | 1943556 A2 | 7/2008 | |
| EP | 2290428 A2 | 3/2011 | |
| EP | 2350774 A1 | 8/2011 | |
| EP | 1237067 B1 | 1/2016 | |
| EP | 3139245 A1 | 3/2017 | |
| EP | 3164776 B1 | 5/2017 | |
| EP | 3236211 A1 | 10/2017 | |
| EP | 2723240 B1 | 8/2018 | |
| EP | 2896986 B1 | 2/2021 | |
| GB | 2499635 A | 8/2013 | |
| GB | 2542853 A | 4/2017 | |
| IN | 938/DEL/2004 A | 6/2006 | |
| JP | H03-036974 U | 4/1991 | |
| JP | H10-333094 A | 12/1998 | |
| JP | 2002-529806 | 9/2002 | |
| JP | 2003-029198 A | 1/2003 | |
| JP | 2003-141574 A | 5/2003 | |
| JP | 2003-228027 A | 8/2003 | |
| JP | 2003-329873 A | 11/2003 | |
| JP | 2005-303843 A | 10/2005 | |
| JP | 2007-012530 A | 1/2007 | |
| JP | 2007-86696 A | 4/2007 | |
| JP | 2007-273733 A | 10/2007 | |
| JP | 2008-257127 A | 10/2008 | |
| JP | 2009-090689 A | 4/2009 | |
| JP | 2009-244869 A | 10/2009 | |
| JP | 2010-014443 A | 1/2010 | |
| JP | 2010-139575 | 6/2010 | |
| JP | 2011-033993 A | 2/2011 | |
| JP | 2011-257203 A | 12/2011 | |
| JP | 2011-530131 A | 12/2011 | |
| JP | 2012-015774 A | 1/2012 | |
| JP | 2012-235036 A | 11/2012 | |
| JP | 2013-525872 A1 | 6/2013 | |
| JP | 2013-206322 A | 10/2013 | |
| JP | 2014-500522 A | 1/2014 | |
| JP | 2014-192550 A | 10/2014 | |
| JP | 2015-191032 A | 11/2015 | |
| JP | 2016-502120 A | 1/2016 | |
| JP | 2016-85463 A | 5/2016 | |
| JP | 2016-516227 A | 6/2016 | |
| JP | 2016-126134 A | 7/2016 | |
| JP | 2017-015697 A | 1/2017 | |
| JP | 2017-153498 | 9/2017 | |
| JP | 2017-531840 A | 10/2017 | |
| JP | 2017-535825 A | 11/2017 | |
| JP | 6232763 B2 | 11/2017 | |
| JP | 6333965 B2 | 5/2018 | |
| KR | 2005-0010775 A | 1/2005 | |
| KR | 10-2006-0059992 A | 6/2006 | |
| KR | 10-2011-0006408 | 1/2011 | |
| KR | 10-1372623 B1 | 3/2014 | |
| KR | 10-2017-0017243 | 2/2017 | |
| TW | 201219829 A | 5/2012 | |
| TW | 201803289 A | 1/2018 | |
| WO | 1991/000565 A2 | 1/1991 | |
| WO | 2000/030368 A1 | 6/2000 | |
| WO | 2002/071315 A2 | 9/2002 | |
| WO | 2004095248 A | 11/2004 | |
| WO | 2006132614 A1 | 12/2006 | |
| WO | WO-2007041678 A2 * | 4/2007 | ............... A61B 5/06 |
| WO | 2007/037089 A1 | 5/2007 | |
| WO | 2007/085682 A1 | 8/2007 | |

(56) References Cited

FOREIGN PATENT DOCUMENTS

| WO | 2007/102144 | A1 | 9/2007 | | |
| --- | --- | --- | --- | --- | --- |
| WO | 2008148927 | A1 | 12/2008 | | |
| WO | 2009/101238 | A1 | 8/2009 | | |
| WO | 2010015807 | A1 | 2/2010 | | |
| WO | 2014203440 | A1 | 12/2010 | | |
| WO | 2012030787 | A2 | 3/2012 | | |
| WO | 2013/049012 | A1 | 4/2013 | | |
| WO | 2013062701 | A1 | 5/2013 | | |
| WO | 2013/145536 | A1 | 10/2013 | | |
| WO | 2014033306 | A1 | 3/2014 | | |
| WO | 2015/079610 | A1 | 6/2015 | | |
| WO | 2015/143641 | A1 | 10/2015 | | |
| WO | 2015143641 | A1 | 10/2015 | | |
| WO | 2015194597 | A1 | 12/2015 | | |
| WO | 2016/054092 | A1 | 4/2016 | | |
| WO | 2017004695 | A1 | 1/2017 | | |
| WO | 2017044761 | A1 | 3/2017 | | |
| WO | 2017049163 | A1 | 3/2017 | | |
| WO | 2017051595 | A1 | 3/2017 | | |
| WO | 2017120475 | A1 | 7/2017 | | |
| WO | 2017176861 | A1 | 10/2017 | | |
| WO | 2017/203201 | A1 | 11/2017 | | |
| WO | 2017203201 | A1 | 11/2017 | | |
| WO | 2018008232 | A1 | 1/2018 | | |
| WO | 2018/031261 | A1 | 2/2018 | | |
| WO | 2018022523 | A1 | 2/2018 | | |
| WO | 2018/044537 | A1 | 3/2018 | | |
| WO | 2018039273 | A1 | 3/2018 | | |
| WO | 2018057564 | A1 | 3/2018 | | |
| WO | 2018085287 | A1 | 5/2018 | | |
| WO | 2018087408 | A1 | 5/2018 | | |
| WO | 2018097831 | A1 | 5/2018 | | |
| WO | 2018166921 | A1 | 9/2018 | | |
| WO | WO-2018236587 | A1 * | 12/2018 | ............. | A61B 34/20 |
| WO | WO-2019040493 | A1 * | 2/2019 | ............. | A61B 34/10 |
| WO | 2019148154 | A1 | 8/2019 | | |
| WO | 2020010226 | A1 | 1/2020 | | |

OTHER PUBLICATIONS

Communication Pursuant to Article 94(3) EPC dated Oct. 21, 2021, European Patent Application No. 16207441.3, (4 pages).
Communication Pursuant to Rule 164(1) EPC dated Jul. 27, 2021, European Patent Application No. 19833664.6, (11 pages).
Extended European Search Report dated Jun. 30, 2021, European Patent Application No. 19811971.1, (9 pages).
Extended European Search Report dated Mar. 4, 2021, European Patent Application No. 19768418.6, (9 pages).
Extended European Search Report dated Jan. 4, 2022, European Patent Application No. 19815085.6, (9 pages).
Extended European Search Report dated Jul. 16, 2021, European Patent Application No. 19810142.0, (14 pages).
Extended European Search Report dated Jul. 30, 2021, European Patent Application No. 19839970.1, (7 pages).
Extended European Search Report dated Oct. 27, 2021, European Patent Application No. 19833664.6, (10 pages).
Extended European Search Report dated Sep. 20, 2021, European Patent Application No. 19851373.1, (8 pages).
Extended European Search Report dated Sep. 28, 2021, European Patent Application No. 19845418.3, (13 pages).
Final Office Action dated Jun. 15, 2021, U.S. Appl. No. 16/928,313, (42 pages).
Final Office Action dated Mar. 1, 2021, U.S. Appl. No. 16/214,575, (29 pages).
Final Office Action dated Sep. 17, 2021, U.S. Appl. No. 16/938,782, (44 pages).
"Multi-core processor", TechTarget, 2013, (1 page).
Non Final Office Action dated Aug. 4, 2021, U.S. Appl. No. 16/864,721, (51 pages).
Non Final Office Action dated Jul. 9, 2021, U.S. Appl. No. 17/002,663, (43 pages).
Non Final Office Action dated Jul. 9, 2021, U.S. Appl. No. 16/833,093, (47 pages).
Non Final Office Action dated Jun. 10, 2021, U.S. Appl. No. 16/938,782, (40 Pages).
Non Final Office Action dated Jun. 29, 2021, U.S. Appl. No. 16/698,588, (58 pages).
Non Final Office Action dated May 26, 2021, U.S. Appl. No. 16/214,575, (19 pages).
Non Final Office Action dated Sep. 20, 2021, U.S. Appl. No. 17/105,848, (56 pages).
Non Final Office Action dated Sep. 29, 2021, U.S. Appl. No. 16/748,193, (62 pages).
Giuseppe, Donato, et al., "Stereoscopic helmet mounted system for real time 3D environment reconstruction and indoor ego-motion estimation", Proc. SPIE 6955, Head- and Helmet-Mounted Displays XIII: Design and Applications, 69550P.
Molchanov, Pavlo, et al., "Short-range FMCW monopulse radar for hand-gesture sensing", 2015 IEEE Radar Conference (RadarCon) (2015), pp. 1491-1496.
Mrad, et al., "A framework for System Level Low Power Design Space Exploration", 1991.
Sheng, Liu, et al., "Time-multiplexed dual-focal plane head-mounted display with a liquid lens", Optics Letters, Optical Society of Amer I Ca, US, vol. 34, No. 11, Jun. 1, 2009 (Jun. 1, 2009), XP001524475, ISSN: 0146-9592, pp. 1642-1644.
"Communication according to Rule 164(1) EPC dated Feb. 23, 2022", European Patent Application No. 20753144.3, (11 pages).
"Communication Pursuant to Article 94(3) EPC dated Apr. 25, 2022", European Patent Application No. 18885707.2, (5 pages).
"Communication Pursuant to Article 94(3) EPC dated May 30, 2022", European Patent Application No. 19768418.6, (6 pages).
"Extended European Search Report dated Jan. 28, 2022", European Patent Application No. 19815876.8, (9 pages).
"Extended European Search Report dated Jun. 19, 2020", European Patent Application No. 20154750.2, (10 pages).
"Extended European Search Report dated Mar. 22, 2022", European Patent Application No. 19843487.0, (14 pages).
"Extended European Search Report dated May 16, 2022", European Patent Application No. 19871001.4, (9 pages).
"Extended European Search Report dated May 30, 2022", European Patent Application No. 20753144.3, (10 pages).
"Final Office Action dated Feb. 23, 2022", U.S. Appl. No. 16/748,193, (23 pages).
"Final Office Action dated Feb. 3, 2022", U.S. Appl. No. 16/864,721, (36 pages).
"Final Office Action dated Jul. 13, 2022", U.S. Appl. No. 17/262,991, (18 pages).
"First Examination Report dated May 13, 2022", Indian Patent Application No. 202047026359, (8 pages).
"First Office Action dated Mar. 14, 2022 with English translation", Chinese Patent Application No. 201880079474.6, (11 pages).
"Non Final Office Action dated Apr. 1, 2022", U.S. Appl. No. 17/256,961, (65 pages).
"Non Final Office Action dated Apr. 11, 2022", U.S. Appl. No. 16/938,782, (52 pages).
"Non Final Office Action dated Apr. 12, 2022", U.S. Appl. No. 17/262,991, (60 pages).
"Non Final Office Action dated Feb. 2, 2022", U.S. Appl. No. 16/783,866, (8 pages).
"Non Final Office Action dated Mar. 31, 2022", U.S. Appl. No. 17/257,814, (60 pages).
"Non Final Office Action dated Mar. 9, 2022", U.S. Appl. No. 16/870,676, (57 pages).
"Non Final Office Action dated May 10, 2022", U.S. Appl. No. 17/140,921, (25 pages).
"Non Final Office Action dated May 17, 2022", U.S. Appl. No. 16/748,193, (11 pages).
"Communication Pursuant to Article 94(3) EPC dated Feb. 28, 2023", European Patent Application No. 19845418.3, (6 Pages).
"Communication Pursuant to Article 94(3) EPC dated Jul. 28, 2023", European Patent Application No. 19843487.0, (15 pages).
"Communication Pursuant to Article 94(3) EPC dated May 23, 2023", European Patent Application No. 18890390.0, (5 pages).

(56) References Cited

OTHER PUBLICATIONS

"Communication Pursuant to Article 94(3) EPC dated Oct. 6, 2023", European Patent Application No. 19851373.1, (6 pages).
"Communication Pursuant to Rule 164(1) EPC dated Feb. 23, 2022", European Patent Application No. 20753144.3, (11 pages).
"Extended European Search Report dated Jan. 8, 2024", European Patent Application No. 23195266.4, (8 pages).
"Final Office Action dated Oct. 16, 2023", U.S. Appl. No. 17/098,043, (7 pages).
"Final Office Action dated Dec. 1, 2023", U.S. Appl. No. 17/357,795, (18 pages).
"Final Office Action dated Sep. 8, 2023 with English translation", Japanese Patent Application No. 2020-566620, (18 pages).
"First Examination Report dated Aug. 8, 2023", Australian Patent Application No. 2018379105, (3 pages).
"First Office Action dated Dec. 12, 2023 with English translation", Japanese Patent Application No. 2021-545712, (8 pages).
"First Office Action dated Dec. 20, 2023 with English translation", Chinese Patent Application No. 201980050600.X, (21 pages).
"First Office Action dated Dec. 27, 2023 with English translation", Chinese Patent Application No. 201980075942.7, (7 pages).
"First Office Action dated Jul. 4, 2023 with English translation", Japanese Patent Application No. 2021-505669, (6 pages).
"First Office Action dated Nov. 2, 2023 with English translation", Chinese Patent Application No. 201980090867.1, (16 pages).
"First Office Action dated Dec. 11, 2023 with translation", Chinese Patent Application No. 201980032005.3, (17 pages).
"First Office Action dated Jun. 13, 2023 with English translation", Japanese Patent Application No. 2020-567853, (7 pages).
"First Office Action dated May 26, 2023 with English translation", Japanese Patent Application No. 2021-500607, (6 pages).
"First Office Action dated May 30, 2023 with English translation", Japanese Patent Application No. 2021-519873, (8 pages).
"First Office Action dated Sep. 29, 2023 with English translation", Japanese Patent Application No. 2023-10887, (5 pages).
"Non Final Office Action dated Nov. 19, 2019", U.S. Appl. No. 16/355,611, (31 pages).
"Non Final Office Action dated Aug. 2, 2023", U.S. Appl. No. 17/807,600, (25 pages).
"Non Final Office Action dated Jul. 20, 2023", U.S. Appl. No. 17/650,188, (11 pages).
"Non Final Office Action dated Jun. 14, 2023", U.S. Appl. No. 17/516,483, (10 pages).
"Non Final Office Action dated Nov. 3, 2023", U.S. Appl. No. 17/416,248, (17 pages).
"Non Final Office Action dated Oct. 11, 2023", U.S. Appl. No. 17/357,795, (14 pages).
"Non Final Office Action dated Oct. 24, 2023", U.S. Appl. No. 17/259,020, (21 pages).
"Notice of Allowance dated Jul. 27, 2023 with English translation", Korean Patent Application No. 10-2020-7019685, (4 pages).
"Office Action dated Nov. 21, 2023 with English Translation", Japanese Patent Application No. 2021-535716, (15 pages).
"Office Action dated Dec. 14, 2023 with English translation", Japanese Patent Application No. 2021-526564, (13 pages).
"Office Action dated Jul. 20, 2023 with English translation", Japanese Patent Application No. 2021-505884, (6 pages).
"Office Action dated Jun. 8, 2023 with English translation", Japanese Patent Application No. 2021-503762, (6 pages).
"Office Action dated Nov. 7, 2023 with English translation", Korean Patent Application No. 10-2023-7036734, (5 pages).
"Office Action dated Nov. 8, 2023 with English translation", Chinese Patent Application No. 201980060018.1, (12 pages).
"Penultimate Office Action dated Oct. 19, 2023 with English translation", Japanese Patent Application No. 2021-509779, (5 pages).
"Second Office Action dated Sep. 25, 2023 with English translation", Japanese Patent Application No. 2020-567853, (8 pages).
"Wikipedia Dioptre", Jun. 22, 2018 (Jun. 22, 2018), XP093066995,Retrieved from the Internet: URL:https://en.wikipedia.org/w/index.php? title=Dioptre&direction=next&oldid=846451540 [retrieved on Jul. 25, 2023], (3 pages).
"Extended European Search Report dated Dec. 14, 2022", European Patent Application No. 20886547.7, (8 pages).
"Extended European Search Report dated Aug. 24, 2022", European Patent Application No. 20846338.0, (13 pages).
"Extended European Search Report dated Aug. 8, 2022", European Patent Application No. 19898874.3, (8 pages).
"Extended European Search Report dated Sep. 8, 2022", European Patent Application No. 20798769.4, (13 pages).
"Extended European Search Report dated Nov. 3, 2022", European Patent Application No. 20770244.0, (23 pages).
"Final Office Action dated Dec. 29, 2022", U.S. Appl. No. 17/098,059, (32 pages).
"First Examination Report dated Jul. 27, 2022", Chinese Patent Application No. 201980036675.2, (5 pages).
"First Examination Report dated Jul. 28, 2022", Indian Patent Application No. 202047024232, (6 pages).
"First Office Action dated Sep. 16, 2022 with English translation", Chinese Patent Application No. 201980063642.7, (7 pages).
"FS_XR5G: Permanent document, v0.4.0", Qualcomm Incorporated, 3GPP TSG-SA 4 Meeting 103 retrieved from the Internet: URL:http://www.3gpp.org/ftp/Meetings%5F3GPP%5FSYNC/SA4/Docs/S4%2DI90526%2Ezip [retrieved on Apr. 12, 2019], Apr. 12, 2019, (98 pages).
"Non Final Office Action dated Dec. 7, 2022", U.S. Appl. No. 17/357,795, (63 pages).
"Non Final Office Action dated Feb. 3, 2023", U.S. Appl. No. 17/429,100, (16 pages).
"Non Final Office Action dated Feb. 3, 2023", U.S. Appl. No. 17/497,965, (32 pages).
"Non Final Office Action dated Jan. 24, 2023", U.S. Appl. No. 17/497,940, (10 pages).
"Non Final Office Action dated Jul. 26, 2022", U.S. Appl. No. 17/098,059, (28 pages).
"Non Final Office Action dated Sep. 19, 2022", U.S. Appl. No. 17/263,001, (14 pages).
"Notice of Reason for Rejection dated Oct. 28, 2022 with English translation", Japanese Patent Application No. 2020-531452, (3 pages).
"Office Action dated Nov. 24, 2022 with English Translation", Japanese Patent Application No. 2020-533730, (11 pages).
"Second Office Action dated Jul. 13, 2022 with English Translation", Chinese Patent Application No. 201880079474.6, (10 pages).
"Second Office Action dated Jun. 20, 2022 with English Translation", Chinese Patent Application No. 201880089255.6, (14 pages).
Anonymous , "Koi Pond: Top iPhone App Store Paid App", https://web.archive.org/web/20080904061233/https://www.iphoneincanada.ca/reviews /koi-pond-top-iphone-app-store-paid-app/—[retrieved on Aug. 9, 2022], (2 pages).
Chittineni, C. , et al., "Single filters for combined image geometric manipulation and enhancement", Proceedings of SPIE vol. 1903, Image and Video Processing, Apr. 8, 1993, San Jose, CA. (Year: 1993), pp. 111-121.
"ARToolKit: Hardware", https://web.archive.org/web/20051013062315/http://www.hitl.washington.edu:80/artoolkit/documentation/hardware.htm (downloaded Oct. 26, 2020), Oct. 13, 2015, (3 pages).
Communication Pursuant to Article 94(3) EPC dated Sep. 4, 2019, European Patent Application No. 10793707.0, (4 pages).
European Search Report dated Oct. 15, 2020, European Patent Application No. 20180623.9, (10 pages).
Examination Report dated Jun. 19, 2020, European Patent Application No. 20154750.2, (10 pages).
Extended European Search Report dated May 20, 2020, European Patent Application No. 20154070.5, (7 pages).
Extended European Search Report dated Jan. 22, 2021, European Patent Application No. 18890390.0, (11 pages).
Extended European Search Report dated Nov. 3, 2020, European Patent Application No. 18885707.2, (7 pages).
Extended European Search Report dated Nov. 4, 2020, European Patent Application No. 20190980.1, (14 pages).
Extended European Search Report dated Jun. 12, 2017, European Patent Application No. 16207441.3, (8 pages).

(56) References Cited

OTHER PUBLICATIONS

Final Office Action dated Aug. 10, 2020, U.S. Appl. No. 16/225,961, (13 pages).
Final Office Action dated Dec. 4, 2019, U.S. Appl. No. 15/564,517, (15 pages).
Final Office Action dated Feb. 19, 2020, U.S. Appl. No. 15/552,897, (17 pages).
Final Office Action dated Mar. 19, 2021, U.S. Appl. No. 16/530,776, (25 pages).
Final Office Action dated Nov. 24, 2020, U.S. Appl. No. 16/435,933, (44 pages).
International Search Report and Written Opinion dated Feb. 12, 2021, International Application No. PCT/US20/60555, (25 pages).
International Search Report and Written Opinion dated Mar. 12, 2020, International PCT Patent Application No. PCT/US19/67919, (14 pages).
International Search Report and Written Opinion dated Aug. 15, 2019, International PCT Patent Application No. PCT/US19/33987, (20 pages).
International Search Report and Written Opinion dated Jun. 15, 2020, International PCT Patent Application No. PCT/US2020/017023, (13 pages).
International Search Report and Written Opinion dated Oct. 16, 2019, International PCT Patent Application No. PCT/US19/43097, (10 pages).
International Search Report and Written Opinion dated Oct. 16, 2019, International PCT Patent Application No. PCT/US19/36275, (10 pages).
International Search Report and Written Opinion dated Oct. 16, 2019, International PCT Patent Application No. PCT/US19/43099, (9 pages).
International Search Report and Written Opinion dated Jun. 17, 2016, International PCT Patent Application No. PCT/FI2016/050172, (9 pages).
International Search Report and Written Opinion dated Feb. 2, 2021, International PCT Patent Application No. PCT/US20/60550, (9 pages).
International Search Report and Written Opinion dated Oct. 22, 2019, International PCT Patent Application No. PCT/US19/43751, (9 pages).
International Search Report and Written Opinion dated Dec. 23, 2019, International PCT Patent Application No. PCT/US19/44953, (11 pages).
International Search Report and Written Opinion dated May 23, 2019, International PCT Patent Application No. PCT/US18/66514, (17 pages).
International Search Report and Written Opinion dated Sep. 26, 2019, International PCT Patent Application No. PCT/US19/40544, (12 pages).
International Search Report and Written Opinion dated Aug. 27, 2019, International PCT Application No. PCT/US2019/035245, (8 pages).
International Search Report and Written Opinion dated Dec. 27, 2019, International Application No. PCT/US19/47746, (16 pages).
International Search Report and Written Opinion dated Dec. 3, 2020, International Patent Application No. PCT/US20/43596, (25 pages).
International Search Report and Written Opinion dated Sep. 30, 2019, International Patent Application No. PCT/US19/40324, (7 pages).
International Search Report and Written Opinion dated Sep. 4, 2020, International Patent Application No. PCT/US20/31036, (13 pages).
International Search Report and Written Opinion dated Jun. 5, 2020, International Patent Application No. PCT/US20/19871, (9 pages).
International Search Report and Written Opinion dated Aug. 8, 2019, International PCT Patent Application No. PCT/US2019/034763, (8 pages).
International Search Report and Written Opinion dated Oct. 8, 2019, International PCT Patent Application No. PCT/US19/41151, (7 pages).
International Search Report and Written Opinion dated Jan. 9, 2020, International Application No. PCT/US19/55185, (10 pages).
International Search Report and Written Opinion dated Feb. 28, 2019, International Patent Application No. PCT/US18/64686, (8 pages).
International Search Report and Written Opinion dated Feb. 7, 2020, International PCT Patent Application No. PCT/US2019/061265, (11 pages).
International Search Report and Written Opinion dated Jun. 11, 2019, International PCT Application No. PCT/US19/22620, (7 pages).
Invitation to Pay Additional Fees dated Aug. 15, 2019, International PCT Patent Application No. PCT/US19/36275, (2 pages).
Invitation to Pay Additional Fees dated Sep. 24, 2020, International Patent Application No. PCT/US2020/043596, (3 pages).
Invitation to Pay Additional Fees dated Oct. 22, 2019, International PCT Patent Application No. PCT/US19/47746, (2 pages).
Invitation to Pay Additional Fees dated Apr. 3, 2020, International Patent Application No. PCT/US20/17023, (2 pages).
Invitation to Pay Additional Fees dated Oct. 17, 2019, International PCT Patent Application No. PCT/US19/44953, (2 pages).
Non Final Office Action dated Aug. 21, 2019, U.S. Appl. No. 15/564,517, (14 pages).
Non Final Office Action dated Jan. 26, 2021, U.S. Appl. No. 16/928,313, (33 pages).
Non Final Office Action dated Jan. 27, 2021, U.S. Appl. No. 16/225,961, (15 pages).
Non Final Office Action dated Jul. 27, 2020, U.S. Appl. No. 16/435,933, (16 pages).
Non Final Office Action dated Jun. 17, 2020, U.S. Appl. No. 16/682,911, (22 pages).
Non Final Office Action dated Jun. 19, 2020, U.S. Appl. No. 16/225,961, (35 pages).
Non Final Office Action dated Mar. 3, 2021, U.S. Appl. No. 16/427,337, (41 pages).
Non Final Office Action dated Nov. 5, 2020, U.S. Appl. No. 16/530,776, (45 pages).
Non Final Office Action dated Oct. 22, 2019, U.S. Appl. No. 15/859,277, (15 pages).
Non Final Office Action dated Sep. 1, 2020, U.S. Appl. No. 16/214,575, (40 pages).
Notice of Allowance dated Mar. 25, 2020, U.S. Appl. No. 15/564,517, (11 pages).
Notice of Allowance dated Oct. 5, 2020, U.S. Appl. No. 16/682,911, (27 pages).
Notice of Reason of Refusal dated Sep. 11, 2020 with English translation, Japanese Patent Application No. 2019-140435, (6 pages).
"Phototourism Challenge", CVPR 2019 Image Matching Workshop. https://image matching-workshop. github.io., (16 pages).
Summons to attend oral proceedings pursuant to Rule 115(1) EPC mailed on Jul. 15, 2019, European Patent Application No. 15162521.7, (7 pages).
Aarik, J. et al., "Effect of crystal structure on optical properties of TiO2 films grown by atomic layer deposition", Thin Solid Films; Publication [online]. May 19, 1998 [retrieved Feb. 19, 2020]. Retrieved from the Internet: <URL: https://www.sciencedirect.com/science/article/pii/S0040609097001351?via%3Dihub>; DOI: 10.1016/S0040-6090(97)00135-1; see entire document, (2 pages).
Altwaijry, et al., "Learning to Detect and Match Keypoints with Deep Architectures", Proceedings of the British Machine Vision Conference (BMVC), BMVA Press, Sep. 2016, [retrieved on Jan. 8, 2021 (Jan. 8, 2021 )] < URL: http://www.bmva.org/bmvc/2016/papers/paper049/index.html >, en lire document, especially Abstract, pp. 1-6 and 9.
Arandjelović, Relja et al., "Three things everyone should know to improve object retrieval", CVPR, 2012, (8 pages).
Azom, , "Silica-Silicon Dioxide (SiO2)", AZO Materials; Publication [Online]. Dec. 13, 2001 [retrieved Feb. 19, 2020]. Retrieved from the Internet: <URL: https://www.azom.com/article.aspx?ArticleID=1114>, (6 pages).
Azuma, Ronald T. , "A Survey of Augmented Reality", Presence: Teleoperators and Virtual Environments 6, 4 (Aug. 1997), 355-385;

(56) References Cited

OTHER PUBLICATIONS https://web.archive.org/web/20010604100006/http://www.cs.unc.edu/~azuma/ARpresence.pdf (downloaded Oct. 26, 2020).

Azuma, Ronald T., "Predictive Tracking for Augmented Reality", Department of Computer Science, Chapel Hill NC; TR95-007, Feb. 1995, 262 pages.

Battaglia, Peter W. et al., "Relational inductive biases, deep learning, and graph networks", arXiv:1806.01261, Oct. 17, 2018, pp. 1-40.

Berg, Alexander C et al., "Shape matching and object recognition using low distortion correspondences", In CVPR, 2005, (8 pages).

Bian, Jiawang et al., "GMS: Grid-based motion statistics for fast, ultra-robust feature correspondence.", In CVPR (Conference on Computer Vision and Pattern Recognition), 2017, (10 pages).

Bimber, Oliver et al., "Spatial Augmented Reality: Merging Real and Virtual Worlds", https://web.media.mit.edu/~raskar/book/BimberRaskarAugmentedRealityBook.pdf; published by A K Peters/CRC Press (Jul. 31, 2005); eBook (3rd Edition, 2007), (393 pages).

Brachmann, Eric et al., "Neural-Guided RANSAC: Learning Where to Sample Model Hypotheses", In ICCV (International Conference on Computer Vision ), arXiv:1905.04132v2 [cs.CV] Jul. 31, 2019, (17 pages).

Butail, et al., "Putting the fish in the fish tank: Immersive VR for animal behavior experiments", In: 2012 IEEE International Conference on Robotics and Automation. May 18, 2012 (May 18, 2012) Retrieved on Nov. 14, 2020 (Nov. 14, 2020) from <http:/lcdcl.umd.edu/papers/icra2012.pdf> entire document, (8 pages).

Caetano, TIBéRIO S et al., "Learning graph matching", IEEE TPAMI, 31(6):1048-1058, 2009.

Cech, Jan et al., "Efficient sequential correspondence selection by cosegmentation", IEEE TPAMI, 32(9):1568-1581, Sep. 2010.

Cuturi, Marco, "Sinkhorn distances: Lightspeed computation of optimal transport", NIPS, 2013, (9 pages).

Dai, Angela et al., "ScanNet: Richly-annotated 3d reconstructions of indoor scenes", In CVPR, arXiv:1702.04405v2 [cs.CV] Apr. 11, 2017, (22 pages).

Deng, Haowen et al., "PPFnet: Global context aware local features for robust 3d point matching", In CVPR, arXiv: 1802.02669v2 [cs.CV] Mar. 1, 2018, (12 pages).

Detone, Daniel et al., "Deep image homography estimation", In RSS Work-shop: Limits and Potentials of Deep Learning in Robotics, arXiv:1606.03798v1 [cs.CV] Jun. 13, 2016, (6 pages).

Detone, Daniel et al., "Self-improving visual odometry", arXiv:1812.03245, Dec. 8, 2018, (9 pages).

Detone, Daniel et al., "SuperPoint: Self-supervised interest point detection and description", In CVPR Workshop on Deep Learning for Visual SLAM, arXiv:1712.07629v4 [cs.CV] Apr. 19, 2018, (13 pages).

Dusmanu, Mihai et al., "D2-net: A trainable CNN for joint detection and description of local features", CVPR, arXiv:1905.03561v1 [cs.CV] May 9, 2019, (16 pages).

Ebel, Patrick et al., "Beyond cartesian representations for local descriptors", ICCV, arXiv:1908.05547v1 [cs.CV] Aug. 15, 2019, (11 pages).

Fischler, Martin A et al., "Random sample consensus: a paradigm for model fitting with applications to image analysis and automated cartography", Communications of the ACM, 24(6): 1981, pp. 381-395.

Gilmer, Justin et al., "Neural message passing for quantum chemistry", In ICML, arXiv:1704.01212v2 [cs.LG] Jun. 12, 2017, (14 pages).

Goodfellow, , "Titanium Dioxide-Titania (TiO2)", AZO Materials; Publication [online]. Jan. 11, 2002 [retrieved Feb. 19, 2020]. Retrieved from the Internet: <URL: https://www.azom.com/article.aspx?Article1D=1179>, (9 pages).

Hartley, Richard et al., "Multiple View Geometry in Computer Vision", Cambridge University Press, 2003, pp. 1-673.

Jacob, Robert J., "Eye Tracking in Advanced Interface Design", Human-Computer Interaction Lab, Naval Research Laboratory, Washington, D.C., date unknown. 2003, pp. 1-50.

Lee, et al., "Self-Attention Graph Pooling", Cornell University Library/Computer Science/ Machine Learning, Apr. 17, 2019 [retrieved on Jan. 8, 2021 from the Internet< URL: https://arxiv.org/abs/1904.08082>, entire document.

Lee, Juho et al., "Set transformer: A frame-work for attention-based permutation-invariant neural networks", ICML, arXiv:1810.00825v3 [cs.LG] May 26, 2019, (17 pages).

Leordeanu, Marius et al., "A spectral technique for correspondence problems using pairwise constraints", Proceedings of (ICCV) International Conference on Computer Vision, vol. 2, pp. 1482-1489, Oct. 2005, (8 pages).

Levola, T., "Diffractive Optics for Virtual Reality Displays", Journal of the SID Eurodisplay 14/05, 2005, XP008093627, chapters 2-3, Figures 2 and 10, pp. 467-475.

Levola, Tapani, "Invited Paper: Novel Diffractive Optical Components for Near to Eye Displays—Nokia Research Center", SID 2006 Digest, 2006 SID International Symposium, Society for Information Display, vol. XXXVII, May 24, 2005, chapters 1-3, figures 1 and 3, pp. 64-67.

Li, Yujia et al., "Graph matching networks for learning the similarity of graph structured objects", ICML, arXiv:1904.12787v2 [cs.LG] May 12, 2019, (18 pages).

Li, Zhengqi et al., "Megadepth: Learning single-view depth prediction from internet photos", In CVPR, fromarXiv: 1804.00607v4 [cs.CV] Nov. 28, 2018, (10 pages).

Libovicky, et al., "Input Combination Strategies for Multi-Source Transformer Decoder", Proceedings of the Third Conference on Machine Translation (WMT). vol. 1: Research Papers, Belgium, Brussels, Oct. 31-Nov. 1, 2018; retrieved on Jan. 8, 2021 (Jan. 8, 2021 ) from < URL: https://doi.org/10.18653/v1/W18-64026 >, entire document, pp. 253-260.

Loiola, Eliane M. et al., "A survey for the quadratic assignment problem", European journal of operational research, 176(2): 2007, pp. 657-690.

Lowe, David G., "Distinctive image features from scale-invariant keypoints", International Journal of Computer Vision, 60(2): 91-110, 2004, (28 pages).

Luo, Zixin et al., "ContextDesc: Local descriptor augmentation with cross-modality context", CVPR, arXiv:1904.04084v1 [cs.CV] Apr. 8, 2019, (14 pages).

Memon, F. et al., "Synthesis, Characterization and Optical Constants of Silicon Oxycarbide", EPJ Web of Conferences; Publication [online]. Mar. 23, 2017 [retrieved Feb. 19, 2020).<URL: https://www.epj-conferences.org/articles/epjconf/pdf/2017/08/epjconf_nanop2017_00002.pdf>; DOI: 10.1051/epjconf/201713900002, (8 pages).

Munkres, James, "Algorithms for the assignment and transportation problems", Journal of the Society for Industrial and Applied Mathematics, 5(1): 1957, pp. 32-38.

Ono, Yuki et al., "LF-Net: Learning local features from images", 32nd Conference on Neural Information Processing Systems (NIPS 2018), arXiv:1805.09662v2 [cs.CV] Nov. 22, 2018, (13 pages).

Paszke, Adam et al., "Automatic differentiation in Pytorch", 31st Conference on Neural Information Processing Systems (NIPS 2017), Long Beach, CA, USA, (4 pages).

PEYRé, Gabriel et al., "Computational Optimal Transport", Foundations and Trends in Machine Learning, 11(5-6):355-607, 2019; arXiv:1803.00567v4 [stat.ML] Mar. 18, 2020, (209 pages).

Qi, Charles R. et al., "Pointnet++: Deep hierarchical feature learning on point sets in a metric space.", 31st Conference on Neural Information Processing Systems (NIPS 2017), Long Beach, CA, USA., (10 pages).

Qi, Charles R et al., "Pointnet: Deep Learning on Point Sets for 3D Classification and Segmentation", CVPR, arXiv:1612.00593v2 [cs.CV] Apr. 10, 201, (19 pages).

RADENOVIć, Filip et al., "Revisiting Oxford and Paris: Large-Scale Image Retrieval Benchmarking", CVPR, arXiv:1803.11285v1 [cs.CV] Mar. 29, 2018, (10 pages).

Raguram, Rahul et al., "A comparative analysis of ransac techniques leading to adaptive real-time random sample consensus", Computer Vision—ECCV 2008, 10th European Conference on Computer Vision, Marseille, France, Oct. 12-18, 2008, Proceedings, Part I, (15 pages).

(56) References Cited

OTHER PUBLICATIONS

Ranftl, RENé et al., "Deep fundamental matrix estimation", European Conference on Computer Vision (ECCV), 2018, (17 pages).
Revaud, Jerome et al., "R2D2: Repeatable and Reliable Detector and Descriptor", In NeurIPS, arXiv:1906.06195v2 [cs.CV] Jun. 17, 2019, (12 pages).
Rocco, Ignacio et al., "Neighbourhood Consensus Networks", 32nd Conference on Neural Information Processing Systems (NeurIPS 2018), Montréal, Canada, arXiv:1810.10510v2 [cs.CV] Nov. 29, 2018, (20 pages).
Rublee, Ethan et al., "ORB: An efficient alternative to Sift or Surf", Proceedings of the IEEE International Conference on Computer Vision. 2564-2571. 2011; 10.1109/ICCV.2011.612654, (9 pages).
Sarlin, et al., "SuperGlue: Learning Feature Matching with Graph Neural Networks", Cornell University Library/Computer Science/Computer Vision and Pattern Recognition, Nov. 26, 2019 [retrieved on Jan. 8, 2021 from the Internet< URL: https://arxiv.org/abs/1911.11763>, entire document.
Sattler, Torsten et al., "SCRAMSAC: Improving RANSAC's efficiency with a spatial consistency filter", ICCV, 2009: 2090-2097., (8 pages).
Schonberger, Johannes L. et al., "Pixelwise view selection for un-structured multi-view stereo", Computer Vision—ECCV 2016: 14th European Conference, Amsterdam, The Netherlands, Oct. 11-14, 2016, Proceedings, Part III, pp. 501-518, 2016.
Schonberger, Johannes L. et al., "Structure-from-motion revisited", Proceedings of the IEEE Conference on Computer Vision and Pattern Recognition (CVPR), 2016, pp. 4104-4113, (11 pages).
Sinkhorn, Richard et al., "Concerning nonnegative matrices and doubly stochastic matrices.", Pacific Journal of Mathematics, 1967, pp. 343-348.
Spencer, T. et al., "Decomposition of poly(propylene carbonate) with UV sensitive iodonium 11 salts", Polymer Degradation and Stability; (online]. Dec. 24, 2010 (retrieved Feb. 19, 2020]., <URL: http:/fkohl.chbe.gatech.edu/sites/default/files/linked_files/publications/2011Decomposition%20of%20poly(propylene%20carbonate)%20with%20UV%20sensitive%20iodonium%20salts,pdf>; DOI: 10,1016/j.polymdegradstab.2010, 12.003, (17 pages).
Tanriverdi, Vildan et al., "Interacting With Eye Movements in Virtual Environments", Department of Electrical Engineering and Computer Science, Tufts University; Proceedings of the SIGCHI conference on Human Factors in Computing Systems, Apr. 2000, pp. 1-8.
Thomee, Bart et al., "YFCC100m: The new data in multimedia research", Communications of the ACM, 59(2):64-73, 2016; arXiv:1503.01817v2 [cs.MM] Apr. 25, 2016, (8 pages).
Torresani, Lorenzo et al., "Feature correspondence via graph matching: Models and global optimization", Computer Vision—ECCV 2008, 10th European Conference on Computer Vision, Marseille, France, Oct. 12-18, 2008, Proceedings, Part II, (15 pages).
Tuytelaars, Tinne et al., "Wide baseline stereo matching based on local, affinely invariant regions", BMVC, 2000, pp. 1-14.
Ulyanov, Dmitry et al., "Instance normalization: The missing ingredient for fast stylization", arXiv:1607.08022v3 [cs.CV] Nov. 6, 2017, (6 pages).
Vaswani, Ashish et al., "Attention is all you need", 31st Conference on Neural Information Processing Systems (NIPS 2017), Long Beach, CA, USA; arXiv:1706.03762v5 [cs.CL] Dec. 6, 2017, (15 pages).
VELIčKOVIč, PETAR et al., "Graph attention networks", ICLR, arXiv:1710.10903v3 [stat.ML] Feb. 4, 2018, (12 pages).
Villani, CéDRIC , "Optimal transport: old and new", vol. 338. Springer Science & Business Media, Jun. 2008, pp. 1-998.
Wang, Xiaolong et al., "Non-local neural networks", CVPR, arXiv:1711.07971v3 [cs.CV] Apr. 13, 2018, (10 pages).
Wang, Yue et al., "Deep Closest Point: Learning representations for point cloud registration", ICCV, arXiv:1905.03304v1 [cs.CV] May 8, 2019, (10 pages).
Wang, Yue et al., "Dynamic Graph CNN for learning on point clouds", ACM Transactions on Graphics, arXiv:1801.07829v2 [cs.CV] Jun. 11, 2019, (13 pages).
Weissel, et al., "Process cruise control: event-driven clock scaling for dynamic power management", Proceedings of the 2002 international conference on Compilers, architecture, and synthesis for embedded systems. Oct. 11, 2002 (Oct. 11, 2002) Retrieved on May 16, 2020 (May 16, 2020) from <URL: https://dl.acm.org/doi/pdf/10.1145/581630.581668>, p. 238-246.
Yi, Kwang M. et al., "Learning to find good correspondences", CVPR, arXiv:1711.05971v2 [cs.CV] May 21, 2018, (13 pages).
Yi, Kwang Moo et al., "Lift: Learned invariant feature transform", ECCV, arXiv:1603.09114v2 [cs.CV] Jul. 29, 2016, (16 pages).
Zaheer, Manzil et al., "Deep Sets", 31st Conference on Neural Information Processing Systems (NIPS 2017), Long Beach, CA, USA; arXiv:1703.06114v3 [cs.LG] Apr. 14, 2018, (29 pages).
Zhang, Jiahui et al., "Learning two-view correspondences and geometry using order-aware network", ICCV; aarXiv:1908.04964v1 [cs.CV] Aug. 14, 2019, (11 pages).
Zhang, Li et al., "Dual graph convolutional net-work for semantic segmentation", BMVC, 2019; arXiv:1909.06121v3 [cs.CV] Aug. 26, 2020, (18 pages).
"Decision of Rejection dated Jan. 5, 2023 with English translation", Chinese Patent Application No. 201880079474.6, (10 pages).
"Extended European Search Report dated Apr. 5, 2023", European Patent Application No. 20888716.6, (11 pages).
"Final Office Action dated Mar. 10, 2023", U.S. Appl. No. 17/357,795, (15 pages).
"First Office Action dated Apr. 21, 2023 with English translation", Japanese Patent Application No. 2021-509779, (26 pages).
"First Office Action dated Apr. 13, 2023 with English Translation", Japanese Patent Application No. 2020-567766, (7 pages).
"First Office Action dated Dec. 22, 2022 with English translation", Chinese Patent Application No. 201980061450.2, (11 pages).
"First Office Action dated Jan. 24, 2023 with English translation", Japanese Patent Application No. 2020-549034, (7 pages).
"First Office Action dated Jan. 30, 2023 with English translation", Chinese Patent Application No. 201980082951.9, (5 pages).
"First Office Action dated Mar. 27, 2023 with English translation", Japanese Patent Application No. 2020-566617, (6 pages).
"First Office Action dated Mar. 6, 2023 with English translation", Korean Patent Application No. 10-2020-7019685, (7 pages).
"Non Final Office Action dated Apr. 13, 2023", U.S. Appl. No. 17/098,043, (7 pages).
"Non Final Office Action dated Mar. 1, 2023", U.S. Appl. No. 18/046,739, (34 pages).
"Non Final Office Action dated May 11, 2023", U.S. Appl. No. 17/822,279, (24 pages).
"Office Action dated Apr. 13, 2023 with English translation", Japanese Patent Application No. 2020-533730, (13 pages).
"Office Action dated Mar. 30, 2023 with English translation", Japanese Patent Application No. 2020-566620, (10 pages).
"Second Office Action dated May 2, 2023 with English Translation", Japanese Patent Application No. 2020-549034, (6 pages).
Li, Yujia , et al., "Graph Matching Networks for Learning the Similarity of Graph Structured Objects", arxiv.org, Cornell University Library, 201 Olin Library Cornell University Ithaca, NY 14853, XP081268608, Apr. 29, 2019.
Luo, Zixin , et al., "ContextDesc: Local Descriptor Augmentation With Cross-Modality Context", 2019 IEEE/CVF Conference on Computer Vision and Pattern Recognition (CVPR), IEEE, XP033686823, DOI: 10.1109/CVPR.2019.00263 [retrieved on Jan. 8, 2020], Jun. 15, 2019, pp. 2522-2531.
Zhang, Zen , et al., "Deep Graphical Feature Learning for the Feature Matching Problem", 2019 IEEE/CVF International Conference on Computer Vision (ICCV), IEEE, XP033723985, DOI: 10.1109/ICCV.2019.00519 [retrieved on Feb. 24, 2020], Oct. 27, 2019, pp. 5086-5095.
"First Office Action mailed Mar. 1, 2024 with English translation", Japanese Patent Application No. 2021-553297, (5 pages).
"First Office Action mailed on Feb. 1, 2024 with English translation", Chinese Patent Application No. 202080018865.4, (9 pages).

(56) References Cited

OTHER PUBLICATIONS

"Non Final Office Action mailed on Feb. 26, 2024", U.S. Appl. No. 18/046,739, (48 pages).
"Office Action mailed on Feb. 19, 2024 with English translation", Korean Patent Application No. 10-2020-7020552, (18 pages).
"Communication Pursuant to Article 94(3) EPC mailed on Feb. 21, 2024", European Patent Application No. 20770244.0, (8 pages).
"Office Action mailed on Feb. 26, 2024 with English translation", Chinese Patent Application No. 201980069194.1, (11 pages).
"Office Action mailed on Mar. 6, 2024 with English translation", Chinese Patent Application No. 201980053016.X, (7 pages).

* cited by examiner

PATIENT VIEWING SYSTEM

CROSS-REFERENCE TO RELATED APPLICATIONS

This is a national phase of International Patent Application No: PCT/US2019/047746, filed on Aug. 22, 2019, which claims priority from U.S. Provisional Patent Application No. 62/721,516, filed on Aug. 22, 2018 and U.S. Provisional Patent Application No. 62/771,534, filed on Nov. 26, 2018, all of which are incorporated herein by reference in their entirety.

BACKGROUND OF THE INVENTION

1). Field of the Invention

This invention relates to a patient viewing system.

2). Discussion of Related Art

Endoscopic catheters are used by surgeons, doctors and other viewers to capture images of body parts within patients. A bronchoscope, for example, is an endoscopic catheter that is used to inspect segmental bronchi. Catheters also serve other functions, such as other endoscopic viewing functions, to treat diseases or to perform surgical procedures.

Because a tip of a catheter is inserted into the body of a patient with minimal or no invasive surgery, the viewer cannot see the location of the tip of the catheter with the naked eye. To assist the viewer, a screen is provided with a combination of images. These images commonly include computed tomography (CT) images that are generated pre-operatively and intraoperatively, along with live video data from a catheter camera in the tip of the catheter. These images are usually provided in different quadrants of the display.

In the case of bronchi, all bronchi tunnels look the same. As a result, a viewer is frequently guessing where the bronchus is that they are currently navigating. Such a viewer will frequently take multiple CT scans as they push the bronchoscope through the bronchi in order to determine where they are in the lungs.

SUMMARY OF THE INVENTION

The invention provides a patient viewing system including a catheter having a lumen and a tip, a tip tracking device that detects movement of the tip, left and right projectors, left and right light wave guides connected to the left and right projectors, a processor, a computer-readable medium connected to the processor, a data store on the computer-readable medium and a set of instructions stored on the computer-readable medium and executable by the processor. The set of instructions may include 1) a catheter tracking system that is connected to the tip tracking device and receives a measurement based on movement detected by the tip tracking device and determines a position of the tip based on the measurement and store the position of the tip in the data store, and 2) a stereoscopic analyzer connected to the data store to receive the image data, the stereoscopic analyzer determining left and right image data sets, the left and right projectors projecting the left and right image data sets respectively, the left and right image data sets differing from one another to give the viewer a perception of a three-dimensional rendering.

The invention further provides a method of viewing a patient including inserting a tip of a catheter into a body of a patient, detecting movement of the tip with a tip tracking device, receiving a measurement based on movement detected by the tip tracking device, determining a position of the tip based on the measurement, storing the position of the tip, determining left and right image data sets based on the position of the tip, generating light in a pattern representative of the position of the tip using left and right projectors projecting the left and right image data sets respectively as light, and guiding the light to retinas of left and right eyes of a viewer so that the viewer sees position of the tip, the left and right image data sets differing from one another to give the viewer a perception of a three-dimensional rendering.

The invention also provides a patient viewing system including a catheter having a lumen and a tip, a tip tracking device that detects movement of the tip, a projector, a light wave guides connected to the projector, a processor, a computer-readable medium connected to the processor, a data store on the computer-readable medium and a set of instructions stored on the computer-readable medium and executable by the processor. The set of instructions may include 1) a catheter tracking system that is connected to the tip tracking device and receives a measurement based on movement detected by the tip tracking device and determines a position of the tip based on the measurement and store the position of the tip in the data store, 2) a past path calculator that stores a past path of the tip in the data store, and 3) a catheter display integrator, the catheter display integrator displaying the past path of the tip together with position of the tip.

The invention further provides a method of viewing a patient including inserting a tip of a catheter into a body of a patient, detecting movement of the tip with a tip tracking device, receiving a measurement based on movement detected by the tip tracking device, determining a position of the tip based on the measurement, storing the position of the tip, determining left and right image data sets based on the position of the tip, generating light in a pattern representative of the position of the tip using left and right projectors projecting the left and right image data sets respectively as light, guiding the light to retinas of left and right eyes of a viewer so that the viewer sees position of the tip, the left and right image data sets differing from one another to give the viewer a perception of a three-dimensional rendering, storing a past path of the tip in the data store, and displaying the past path of the tip together with position of the tip.

The invention also provides a patient viewing system including a catheter having a lumen and a tip, a tip tracking device that detects movement of the tip, a projector, a light wave guides connected to the projector, a processor, a computer-readable medium connected to the processor, a data store on the computer-readable medium and a set of instructions stored on the computer-readable medium and executable by the processor. The set of instructions may include 1) a catheter tracking system that is connected to the tip tracking device and receives a measurement based on movement detected by the tip tracking device and determines a position of the tip based on the measurement and store the position of the tip in the data store, 2) a prospective path calculator that calculates a future path of the tip based the position of the tip, the catheter display integrator displaying the future path, and 3) a catheter display integrator, the catheter display integrator displaying the future path of the tip together with position of the tip.

The invention further provides a method of viewing a patient including inserting a tip of a catheter into a body of a patient, detecting movement of the tip with a tip tracking device, receiving a measurement based on movement detected by the tip tracking device, determining a position of the tip based on the measurement, storing the position of the tip, determining left and right image data sets based on the position of the tip, generating light in a pattern representative of the position of the tip using left and right projectors projecting the left and right image data sets respectively as light, guiding the light to retinas of left and right eyes of a viewer so that the viewer sees position of the tip, the left and right image data sets differing from one another to give the viewer a perception of a three-dimensional rendering, calculating a future path of the tip based the position of the tip, and displaying the future path of the tip together with position of the tip.

The invention also provides a patient viewing system including a transmitter, an energy source connected to the transmitter to activate the transmitter, a body of a patient being positionable relative to the transmitter for the transmitter to generate a forward wave at a body part within the body, a receiver positionable relative to the body to detect a return wave from the body part, the return wave from the body part being in response to the forward wave created by the transmitter, a processor, a computer-readable medium connected to the processor, a data store on the computer-readable medium and a set of instructions stored on the computer-readable medium and executable by the processor. The set of instructions may include 1) a raw data reception unit that receives raw data of the return wave detected by the receiver and stores the raw data in the data store, 2) an image generation unit connected to the data store to process the raw data of the return wave to create image data representing an image and store the image data in the data store, 3) an image data reception unit that receives the image data from the data store, 4) a projector connected to the image data reception unit to receive the image data, the projector generating light in a pattern representative of the image data, and 5) a light wave guide connected to the projector to guide the light to a retina of an eye of a viewer while light from an external surface of the body transmits to the retina of the eye so that the viewer sees the external surface of the body augmented with a rendering of the body part.

The invention further provides a method of viewing a patient including activating a transmitter to generate a forward wave at a body part within the body, detecting, with a receiver, a return wave from the body part, the return wave from the body part being in response to the forward wave created by the transmitter, receiving raw data of the return wave detected by the receiver, storing the raw data in a data store, processing the raw data of the return wave to create image data representing an image, storing the image data in the data store, receiving the image data from the data store, generating light in a pattern representative of the image data, and guiding the light to a retina of an eye of a viewer while light from an external surface of the body transmits to the retina of the eye so that the viewer sees the external surface of the body augmented with a rendering of the body part.

BRIEF DESCRIPTION OF THE DRAWINGS

The invention is further described by way of example with reference to the accompanying drawings, wherein.

DETAILED DESCRIPTION OF THE INVENTION

Figure 1:
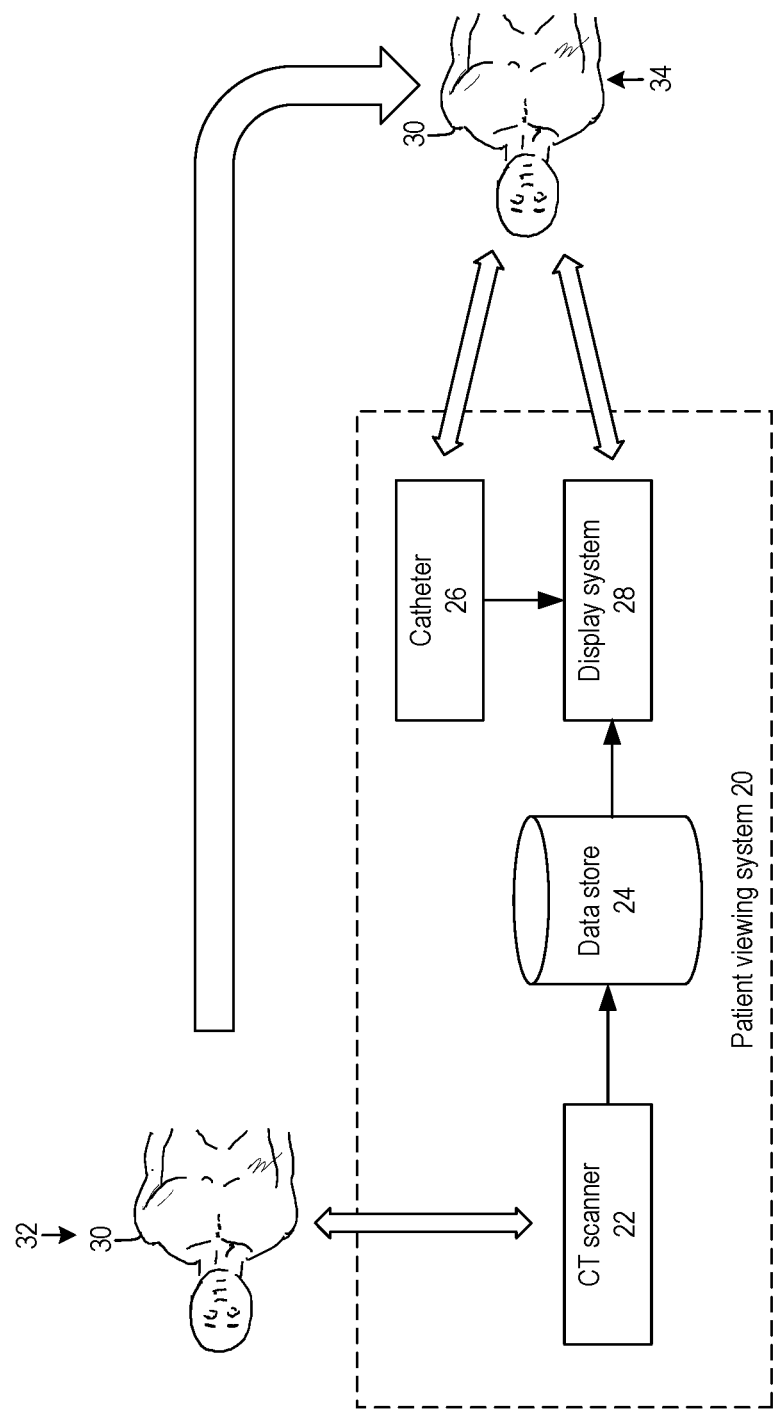
FIG. 1 is a block diagram of a patient viewing system according to an embodiment of the invention.

FIG. 1 of the accompanying drawings illustrates a patient viewing system 20, according to an embodiment of the invention, that includes a CT scanner 22, a data store 24, a catheter 26, and a display system 28.

The data store 24 is connected to the CT scanner 22. Raw data from the CT scanner 22 may be stored in the data store 24. The data store 24 also stores image data that is based on the raw data.

The display system 28 is connected to the data store 24 to be able to retrieve the image data from the data store 24. The catheter 26 is connected to the display system 28 so that the display system 28 can retrieve measurement and video data from the catheter 26 for further processing or for display to a viewer.

In use, a patient is located at a station 32 at the CT scanner 22. A body 30 of the patient is scanned with the CT scanner 22 to obtain raw data that the CT scanner 22 stores in the data store 24. The raw data is then processed to obtain 3D image data.

The patient is transferred from the station 32 at the CT scanner 22 to a station 34 at the display system 28. A viewer uses the display system 28 to view the body 30 of the patient. The display system 28 also retrieves the image data from the data store 24. The viewer uses the display system 28 to view an image in the form of a 3D rendering of the body 30 of the patient. The viewer inserts the catheter 26 into the body 30. The display system 28 retrieves data from a tip of the catheter 26 for further processing or for display to the viewer.

Figure 2:
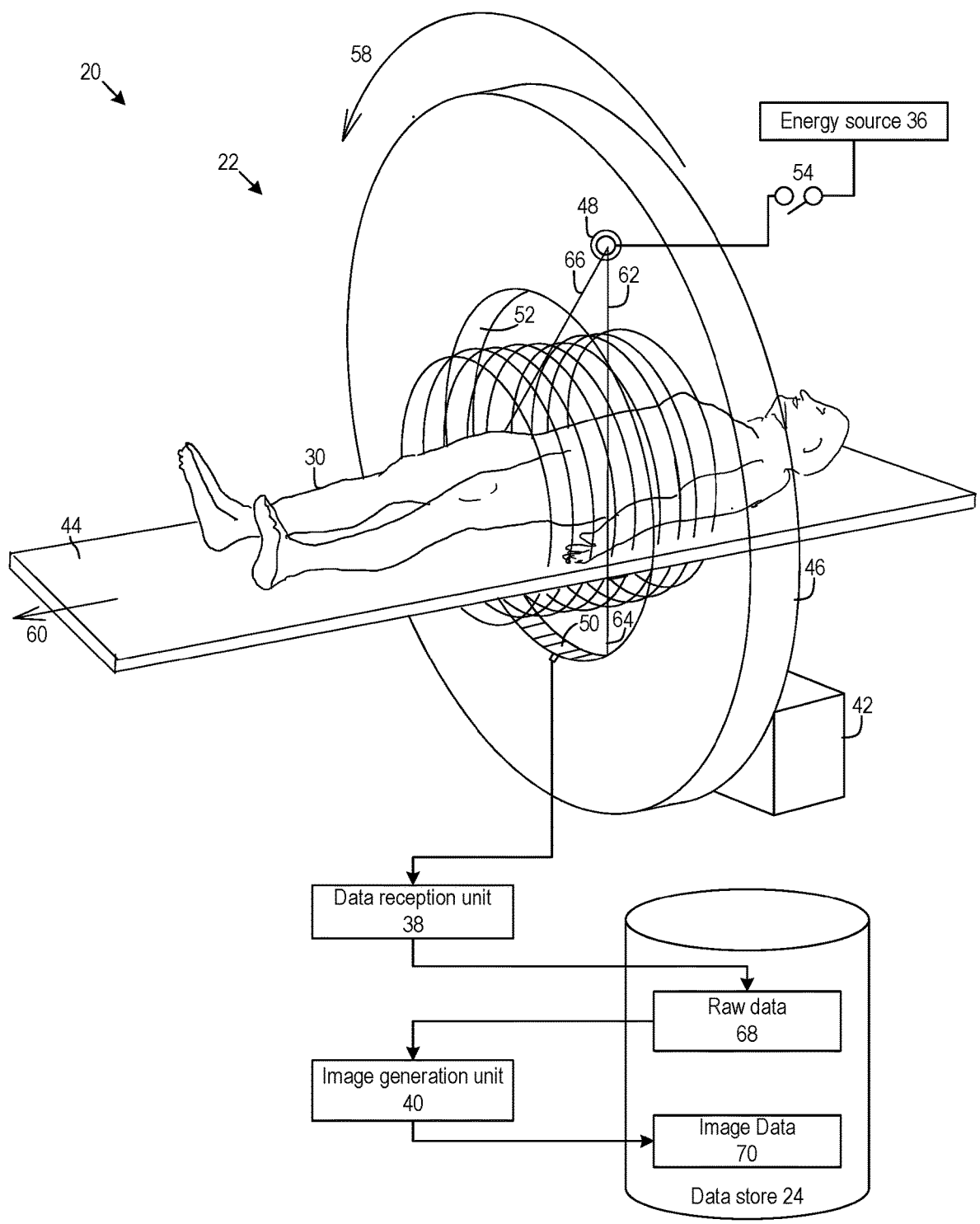
FIG. 2 is a partial perspective view and partial block diagram of a CT scanner, a data reception unit, an image generation unit and a data store forming part of the patient viewing system, according to some embodiments.

FIG. 2 illustrates components of the patient viewing system 20, including the CT scanner 22, the data store 24, an energy source 36, a data reception unit 38, and an image generation unit 40, according to some embodiments.

The CT scanner 22 includes a base 42, a platform 44, a rotor 46, an x-ray transmitter 48, and a plurality of x-ray detectors 50.

The platform 44 is secured to the base 42 through a mechanism (not shown) that permits translational movement of the platform 44 relative to the base 42. An actuator such as a stepper motor (not shown) is operable to cause translational movement of the platform 44 relative to the base 42.

The rotor 46 has an opening 52. The x-ray transmitter 48 is secured to the rotor 46 on one side of the opening 52 and the x-ray detectors 50 are secured to the rotor 46 on an opposing side of the opening 52. The rotor 46 is mounted to the base 42 around the platform 44. The platform 44 moves relative to the opening 52 during its translational movement. A motor (not shown) is connected between the base 42 and the rotor 46 and is operable to rotate the rotor 46 around the platform 44.

The energy source 36 may be connected to the x-ray transmitter 48 through a switch 54. The x-ray detectors 50 are connected to the data reception unit 38. The data reception unit 38 may be a software unit that resides on a computer-readable medium of a computer. The data store 24 resides on the computer-readable medium. The computer-readable medium may be a single computer-readable medium or may be separated within one personal computer or a number of personal computers that are connected to one another on a network. The data reception unit 38 is connected to the data store 24, either directly or over a network.

The image generation unit 40 may be a computer program that resides on the computer-readable medium. The image generation unit 40 is connected to the data store 24, either directly or over a network.

In use, an operator of the CT scanner 22 places the patient with their body 30 laying on the platform 44. The motor connected between the base 42 and the rotor 46 is then switched on so that the rotor 46 rotates in a direction 58 about the platform 44 and the body 30 of the patient. The operator also switches the motor on that moves the platform 44 in a translation direction relative to the base 42 so that the platform 44 moves in a direction 60 relative to the rotor 46. The operator then connects the switch 54 between the energy source 36 and the x-ray transmitter 48 to activate the x-ray transmitter 48. The x-ray transmitter then generates a forward x-ray wave 62.

The body 30 of the patient is positioned relative to the x-ray transmitter 48 so that the forward x-ray wave 62 penetrates the body 30 to a body part (not shown) within the body 30. For purposes of this example, the body parts that are scanned are the lungs of a patent. A lung has many bronchi through which a catheter can travel. It may also be possible for a catheter to travel though hollow passages in the heart, arteries and veins of the blood circulation system etc. The system described herein may also find application for viewing internal body parts without the use of a catheter for vision, surgery or intervention, for example for viewing a growth within the abdomen, for analyzing the internal functioning of a knee, etc. The body part reduces the energy of the forward x-ray wave 62. Different materials within the body part reduce the energy by different amounts. One of the x-ray detectors 50 is positioned relative to the body 30 to detect a return x-ray wave 64 from the body part. The return x-ray wave 64 from the body part is being detected in response to the forward x-ray wave 62 and is essentially the forward x-ray wave 62 that has reduced power because of the reduction in the power by the body part. Further forward x-ray wave 66 is also illustrated. The further x-ray waves are generated between the forward x-ray waves 62 and 66 and are detected by respective ones of the x-ray detectors 50. In this manner, return x-ray waves are received from different parts of the body part.

The x-ray transmitter 48 and x-ray detectors 50 rotate together with the rotor 46 around the body part within the body 30 of the patient. In this manner, the body part may be scanned from different angles to create a two-dimensional "slice" of the anatomy. CT scans are capable of showing bone, organs, soft tissue. Subsequent slices are taken by moving the platform 44 in the direction 60. Each slice thus represents two-dimensional data and the slices together represent data in three-dimensions of the body part.

The data reception unit 38 receives raw data of the return x-ray wave 64 from the x-ray detectors 50. The raw data includes a time sequenced correlation between an angle of the x-ray transmitter 48 relative to the body part within the body 30 of the patient, an energy detected by each one of the x-ray detectors 50, the location of each one of the x-ray detectors 50, and a position of the platform 44. The data reception unit 38 stores the raw data as raw data 68 of the return x-ray wave detected by the x-ray detectors 50.

When enough raw data 68 of the body part is collected, the operator disconnects the switch 54 and stops the platform 44. The operator then stops the rotor 46 and removes the patient from the platform 44.

The image generation unit 40 retrieves the raw data 68 from the data store 24. The image generation unit 40 generates image data based on the raw data 68. The image data includes a three-dimensional rendering of the body part. The image generation unit 40 then stores the image data as image data 70 in the data store 24. The data store 24 may be a single data store or may be distributed between platforms, and as such, the raw data 68 and the image data 70 can be located within a single data store within a personal computer or within several data stores within several personal computers.

Figure 3:
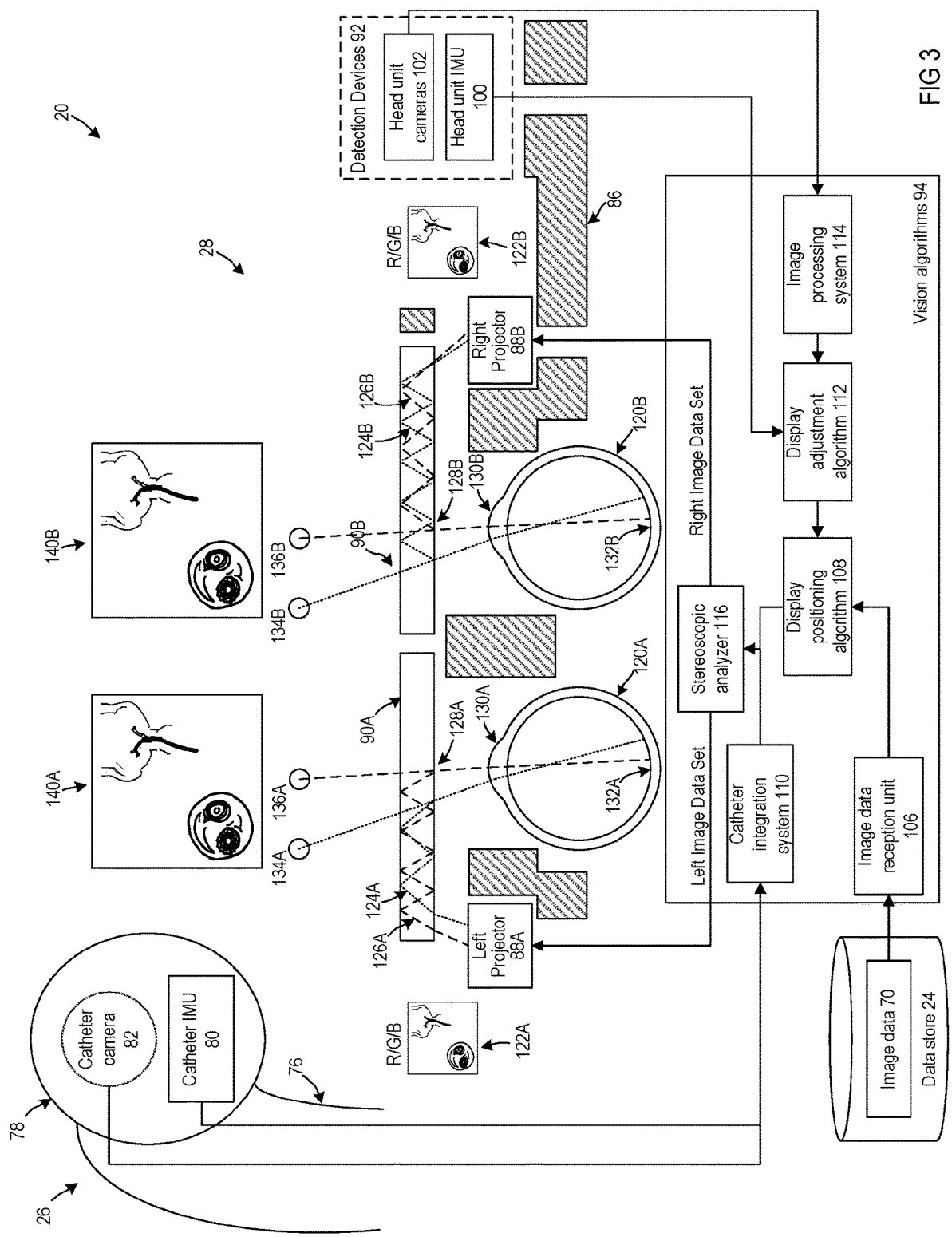
FIG. 3 is a partial perspective view and partial block diagram of a display system, a catheter and a data store forming part of the patient viewing system, according to some embodiments.

FIG. 3 illustrates components of the patient viewing system 20 in more detail, and shows the data store 24

(holding the image data 70), the catheter 26, and the display system 28, according to some embodiments.

The catheter 26 includes a lumen 76 and a tip 78 attached to an end of the lumen 76. The lumen is an elongate member (e.g. the cavity of a tubular part) that forms most of the length of the catheter 26. The lumen 76 includes a mechanism (not shown) that is operable to move the tip 78 in at least four orthogonal directions and all directions in between the orthogonal directions. The tip 78 is thus steerable with the mechanism in the lumen 76. The lumen has a hollow bore that is sufficiently large to hold the mechanism that is used to steer the tip together with any electrical cables and/or an optic fiber that may be required for relaying signals from the tip through the lumen 76 to the display system 28.

The catheter 26 further includes a catheter inertial motion unit (IMU) 80 and a catheter camera 82 secured to the tip 78. The catheter IMU 80 may for example be a semiconductor chip that has a number of measurement devices formed therein. The measurement devices include one or more gyroscopes and one or more accelerometers. Measurements from the gyroscopes and accelerometers, individually or in combination, provide data that indicates movement of the tip 78. Such movement can be tracked in six degrees of freedom, for example translation in x-, y- and z-directions and rotation about x-, y-, and z-axes.

The catheter camera 82 has a lens (not shown) on the side of the tip 78 opposing the lumen 76. The catheter camera 82 is positioned to capture images in the form of live video data in an area in front of the tip 78, i.e. on a side opposing the lumen 76. There may be multiple light sources and multiple cameras on different sides of the tip of the camera, although for ease of discussion it will be assumed that there is only a single camera, for example a built-in camera and light source on a distal end of the catheter.

The display system 28 includes a head-mountable frame 86, left and right projectors 88A and 88B, left and right wave guides 90A and 90B, detection devices 92, and vision algorithms 94. The left and right projectors 88A and 88B, left and right wave guides 90A and 90B and the detection devices 92 are secured to the head-mountable frame 86. The head-mountable frame 86 is shaped to be mounted to a head of a viewer. Components of the head-mountable frame 86 may, for example, include a strap (not shown) that wraps around the back of a head of a viewer.

The left and right projectors 88A and 88B are connected to power supplies. Each projector 88A or 88B has a respective input for image data to be provided to the respective projector 88A or 88B. The respective projector 88A or 88B, when powered, generates light in a two-dimensional pattern and emanates the light therefrom. The left and right wave guides 90A and 90B are positioned to receive the light from the left and right projectors 88A and 88B, respectively. The left and right wave guides 90A and 90B are transparent wave guides.

The detection devices 92 include a head unit IMU 100 and one or more head unit cameras 102. The head unit IMU 100 includes one or more gyroscopes and one or more accelerometers. The gyroscopes and accelerometers are typically formed in a semiconductor chip and are capable of detecting movement of the head unit IMU 100 and the head-mountable frame 86, including movement along three orthogonal axes and rotation about three orthogonal axes.

The head unit cameras 102 continually capture images from an environment around the head-mountable frame 86. The images can be compared to one another to detect movement of the head-mountable frame 86 and the head of the viewer.

The vision algorithms 94 include an image data reception unit 106, a display positioning algorithm 108, a catheter integration system 110, a display adjustment algorithm 112, an image processing system 114, and a stereoscopic analyzer 116. The image data reception unit 106 is connected to the data store 24 through a direct connection or over a network. The components of the vision algorithm 94 are linked to one another through subroutines or calls. Through such subroutines and calls, the image data reception unit 106 is linked via the display positioning algorithm 108 to the stereoscopic analyzer 116.

The catheter integration system 110 may be connected to the catheter IMU 80 and the catheter camera 82 through conductors in the lumen 76. One of ordinary skill in the art will appreciate that the vision algorithms 94 reside on a computing system and that the catheter integration system 110 receives signals from the catheter camera 82 and the catheter IMU 80 and that such signals may convert from analog or digital data to computer software data. The catheter integration system 110 may be connected through subroutines or calls to the stereoscopic analyzer 116.

The display adjustment algorithm 112 and the image processing system 114 are connected to the head unit IMU 100 and the head unit cameras 102 respectively. Such connections are through conductors and, where applicable, through inverters that convert analog or digital data to computer software data. The display adjustment algorithm 112 may be connected through subroutines and calls to the display positioning algorithm 108. The image processing system 114 may be connected though calls and subroutines to the display adjustment algorithm 112.

In use, a viewer mounts the head-mountable frame 86 to their head. The left and right wave guides 90A and 90B are then located in front of left and right eyes 120A and 120B of the viewer.

The image data reception unit 106 retrieves the image data 70 from the data store 24 and provides the image data 70 to the display positioning algorithm 108. The display positioning algorithm 108 enters the image data 70 into the stereoscopic analyzer 116. The image data 70 is three-dimensional image data of the body part as described above. The stereoscopic analyzer 116 analyzes the image data 70 to determine left and right image data sets based on the image data 70. The left and right image data sets are data sets that represent two-dimensional images that differ slightly from one another for purposes of giving the viewer a perception of a three-dimensional rendering. The image data 70 is a static data set which does not change over time.

The stereoscopic analyzer 116 enters the left and right image data sets in to the left and right projectors 88A and 88B. The left and right projectors 88A and 88B then create left and right light patterns 122A and 122B. The components of the display system 28 are shown in plan view and the left and right light patterns 122A and 122B are shown in front elevation views. Each light pattern 122A and 122B includes a plurality of pixels. For purposes of illustration, light rays 124A and 126A from two of the pixels are shown leaving the left projector 88A and entering the left wave guide 90A. The light rays 124A and 126A reflect from sides of the left wave guide 90A. It is shown that the light rays 124A and 126A propagate through internal reflection from left to right within the left wave guide 90A, although it should be understood that the light rays 124A and 126A also propagate in a direction into the paper using refractory and reflective systems. The light rays 124A and 126A exit the left light wave guide 90A through a pupil 128A and then enter the left eye 120A through a pupil 130A of the left eye. The light rays 124A and 126A then fall on a retina 132A of the left eye 120A. In this manner, the left light pattern 122A falls on the retina 132A of the left eye 120A. The viewer is given the perception that the pixels that are formed on the retina 132A are pixels 134A and 136A that the viewer perceives to be at some distance on a side of the left wave guide 90A opposing the left eye 120A.

In a similar manner, the stereoscopic analyzer 116 enters the right image data set into the right projector 88B. The right projector 88B transmits the right light pattern 122B, which is represented by pixels in the form of light rays 124B and 126B. The light rays 124B and 126B reflect within the right wave guide 90B and exit through a pupil 128B. The light rays 124B and 126B then enter through a pupil 130B of the right eye 120B and fall on a retina 132B of the right eye 120B. The pixels of the light rays 124B and 126B are perceived as pixels 134B and 136B behind the right light wave guide 90B.

The patterns that are created on the retinas 132A and 132B are individually perceived as left and right images 140A and 140B that are shown in front elevation view. The left and right images 140A and 140B differ slightly from one another due to the functioning of the stereoscopic analyzer 116. The left and right images 140A and 140B are perceived in a mind of the viewer as a three-dimensional rendering.

As mentioned, the left and right wave guides 90A and 90B are transparent. Light from a real-life object on a side of the left and right wave guides 90A and 90B opposing the eyes 120A and 120B can project through the left and right wave guides 90A and 90B and fall on the retinas 132A and 132B. In particular, light from a surface of the body 30 of the patient falls on the retinas 132A and 132B so that the viewer can see the surface of the body 30 of the patient. An augmented reality is created wherein the surface of the body 30 of the patient that the viewer sees is augmented with a three-dimensional rendering that is perceived by the viewer due to the left and right images 140A and 140B that are, in combination, perceived by the viewer.

The head unit IMU 100 detects every movement of the head of the viewer. Should the viewer, for example, move counterclockwise around the body 30 of the patient and simultaneously rotate their head counterclockwise to continue to see the body 30 of the patient, such movement will be detected by the gyroscopes and accelerometers in the head unit IMU 100. The head unit IMU 100 provides the measurement from the gyroscopes and accelerometers to the display adjustment algorithm 112. The display adjustment algorithm 112 calculates a placement value and provides the placement value to the display positioning algorithm 108. The display positioning algorithm 108 modifies the image data 70 to compensate for movement of the head of the viewer. The display positioning algorithm 108 provides the modified image data 70 to the stereoscopic analyzer 116 for display to the viewer.

The head unit cameras 102 continually capture images as the viewer moves their head. The image processing system 114 analyzes the images by identifying images of objects within the image. The image processing system 114 analyzes movement of the objects to determine a pose position of the head-mountable frame 86. The image processing system 114 provides the pose position to the display adjustment algorithm 112. The display adjustment algorithm 112 uses the pose position to further refine the placement value that the display adjustment algorithm 112 provides to the display positioning algorithm 108. The display positioning algorithm 108 thus modifies the image data 70 based on a combination of motion sensors in the head unit IMU 100 and images taken by the head unit cameras 102.

The catheter integration system 110 may detect a location of the tip 78 of the catheter 26 before the viewer inserts the tip 78 in to the body 30 of the patient. The viewer subsequently inserts the tip 78 in to the body 30 of the patient. The tip 78 is then not visible to the viewer. The catheter IMU 80 provides signals to the catheter integration system 110 that indicate every movement of the tip 78. The catheter integrations system 110 can thus track the position of the tip 78 using the motion sensors in the catheter IMU 80. Unlike the image data 70 that is static, the position of the tip 78 changes over time. The catheter integration system 110 provides the position of the tip 78 to the stereoscopic analyzer 116. The position of the tip 78 may be dynamic in that it changes over time and moves in three-dimensions. The stereoscopic analyzer 116 positions the tip 78 within the left and right image data sets that are inserted into the left and right projectors 88A and 88B. The viewer can thus see the location in the tip 78 within the left and right images 140A and 140B. The location of the tip 78 varies slightly within the left and right images 140A and 140B so that the viewer perceives the location of the tip 78 in three-dimensions. The rendering of the location of the tip 78 as provided by the left and right images 140A and 140B changes over time as the tip 78 makes its way through the body 30 of the patient. Such movement of the location of tip 78 as a rendering changes in three-dimensions so that the viewer perceives the rendering of the tip 78 as moving in three-dimensions, i.e. left, right, up, down, forward, backward, etc.

The catheter camera 82 continues to capture video data and provides the video data to the catheter integration system 110. The catheter integration system 110 provides the video data to the stereoscopic analyzer 116. The stereoscopic analyzer 116 places the video data at a fixed location within the view of the viewer unless or until a user interaction event is detected indicating the location should change. The video data changes over time as different images are captured by the catheter camera 82.

The vision algorithms 94 are a set of instructions that are stored together with the data store 24 on a computer-readable medium. The set of instructions are executable by a processor to carry out the method described above. The computer-readable medium that stores the vision algorithms 94 may be located on a belt pack worn by the viewer.

Figure 4:
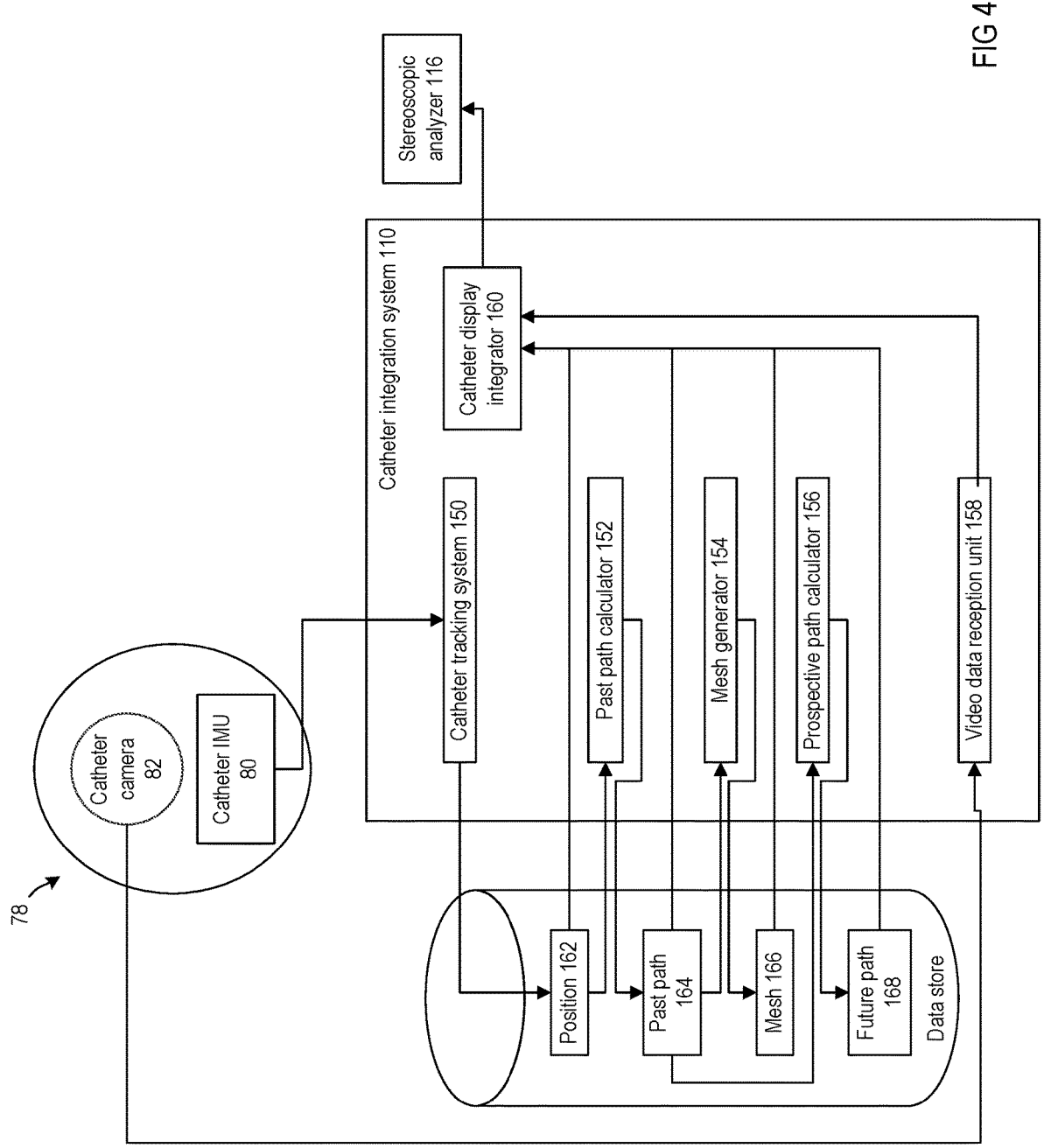
FIG. 4 is a block diagram illustrating a catheter integration system forming part of the display system in FIG. 3 and further illustrates the catheter, according to some embodiments.

FIG. 4 illustrates components of the patient viewing system 20 in more detail, in particular, components of the catheter integration system 110 and their relationship with the catheter IMU 80 and the catheter camera 82 in the tip 78 and the stereoscopic analyzer 116.

The catheter integration system 110 includes a catheter tracking system 150, a past path calculator 152, a mesh generator 154, a prospective path calculator 156, a video data reception unit 158, and a catheter display integrator 160. The catheter tracking system 150 is connected to the catheter IMU 80. The catheter tracking system 150 calculates a position of the tip 78 based on movement detected by the catheter IMU 80. The catheter IMU 80 includes a number of tip tracking devices, including a number of gyroscopes and accelerometer to track its movement in six degrees of freedom. The catheter tracking system 150 stores a current position of the tip 78 as a position 162 in the data store 24. The catheter tracking system 150 continues to monitor the catheter IMU 80, continues to calculate a current position of the tip 78, and continues to store a current position of the tip 78 as a current position 162 in the data store 24.

The catheter display integrator 160 receives the current position 162 from the data store 24 and provides the current position 162 to the stereoscopic analyzer 116. The stereoscopic analyzer 116 displays the current position 162 of the tip 78 as a rendering to the viewer so that the viewer can see the position of the tip 78 as a rendering in three-dimensions.

Past path calculator 152 retrieves every position 162 at every moment in time from the data store 24. The past path calculator 152 calculates a past path of the tip 78 in three-dimensions and stores the past path as a past path 164 in the data store 24. The catheter display integrator 160 receives the past path 164 from the data store 24 and provides the past path 164 to the stereoscopic analyzer 116. The stereoscopic analyzer 116 displays the past path 164 to the viewer as a three-dimensional rendering.

The mesh generator 154 retrieves the past path 164 from the data store and generates a three-dimensional mesh around the past path 164. The mesh generator 154 then stores the mesh as a mesh 166 in the data store 24. The catheter display integrator 160 retrieves the mesh 166 from the data store 24 and provides the mesh 166 to the stereoscopic analyzer 116. The stereoscopic analyzer 116 displays the mesh 166 to the viewer. The stereoscopic analyzer 116 creates a three-dimensional rendering of the mesh 166 that, in some embodiments, overlays the past path 164.

The perspective path calculator 156 retrieves every position 162 of the tip 78 from the data store 24 and calculates a future path of the tip 78 based on the position 162 and past positions retrieved from the data store 24. The perspective path calculator 156 then stores the future path as a future path 168 in the data store 24. The catheter display integrator 160 retrieves the future path 168 from the data store 24 and provides the future path 168 to the stereoscopic analyzer 116. The stereoscopic analyzer 116 displays the future path 168 to the viewer as a three-dimensional rendering.

The video data reception unit 158 receives live video from the catheter camera 82. The video data reception unit 158 provides the live video data to the catheter display integrator 160. The catheter display integrator 160 provides the live video data to the stereoscopic analyzer 116. The stereoscopic analyzer 116 displays the live video data to the viewer. The live video data is a two-dimensional display that is displayed to the viewer at a certain predetermined distance in three-dimensional space. The catheter display integrator also integrates the mesh 166 with the video data from the video data reception unit 158 so that the mesh 166 is displayed on the video data. As the video data changes, with a changing position of the catheter 26 within the body 30 of the patient, the mesh 166 also changes accordingly.

Figure 5:
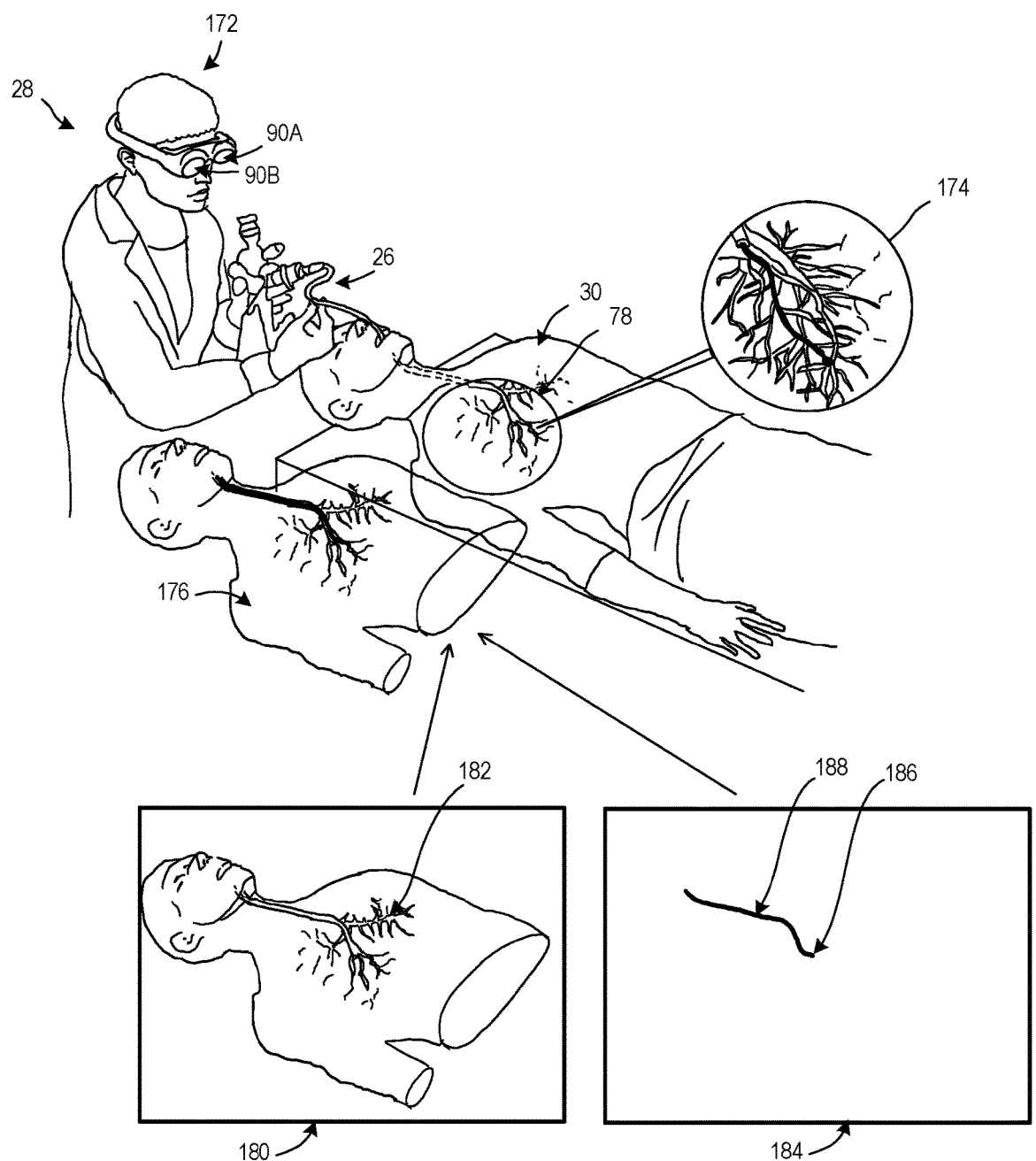
FIG. 5 is a perspective view illustrating a viewer in the form of a surgeon, the viewer seeing a body of a patient and a rendering of a body part inside the patient and further seeing a rendering of a tip of a catheter and a past path of the tip, according to some embodiments.

FIG. 5 illustrates the use of the patient viewing system 20 as hereinbefore described by a viewer 172 in the form of a surgeon who uses the catheter 26 as a bronchoscope for purposes of examining a body part 174 comprising segmental bronchi in lungs of a patient, according to some embodiments.

The viewer 172 can see the body 30 of the patient through the left and right wave guides 90A and 90B. The body part 174 is inside the body 30 of the patient, thus the viewer cannot see the real (i.e. physical) body part 174.

The viewer 172 also sees a three-dimensional rendering 176 which is based on the image data 70 as hereinbefore described. In the particular embodiment, the rendering 176 is located next to the body 30 of the patient. The rendering 176 is included in the figure to show the location where the viewer 172 perceives the rendering 176 relative to the body 30 of the patient, although it will be understood that, from the viewpoint of the reader of this document, the rendering 176 does not exist in the real world. The insert 180 shows that the viewer 172 can see a three-dimensional rendering 182 of the body part 174 as part of the rendering 176.

The viewer 172 inserts the tip 78 of the catheter 26 into a mouth of the patient. The viewer 172 then progresses the tip 78 into the body part 174. The locations of the tip 78 are monitored at instances that are closely spaced in time as hereinbefore described, and its past path is stored in three-dimensions. Sampling times may vary depending on the use case, and optimizations are possible, such as only capturing data while the endoscope is inside the patient's body, or after the user activates a "start recording/sampling" feature. The insert 184 shows that the rendering 176 includes a rendering 186 of the location of the tip 78 in three-dimensions and a rendering 188 of the past path of the tip 78 in three-dimensions. The renderings 182, 186, and 188 may be displayed to the viewer 172 simultaneously so that the viewer sees the renderings 186 and 188 within the rendering 182.

Figure 6:
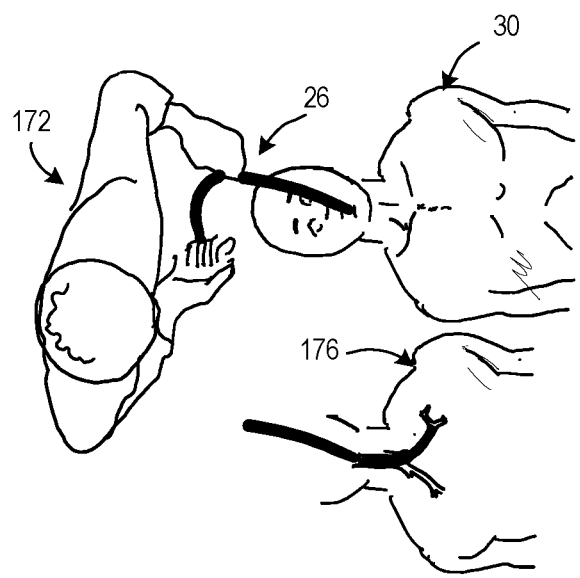
FIG. 6 is top plan view of FIG. 5, according to some embodiments.

FIG. 6 is a top plan view showing a location of the viewer 172 relative to the body 30 of the patient and further illustrates the location of the rendering 176 within the view of the viewer 172, according to some embodiments. The rendering 176 may be placed in any position relative to the body 30 of the patient, based on user preference, pre-programmed default settings, or any other suitable means. The particular relative location of body 30 of the patient to the rendering 176 in FIG. 6 is for illustration purposes only and should in no way be considered limiting.

Figure 7:
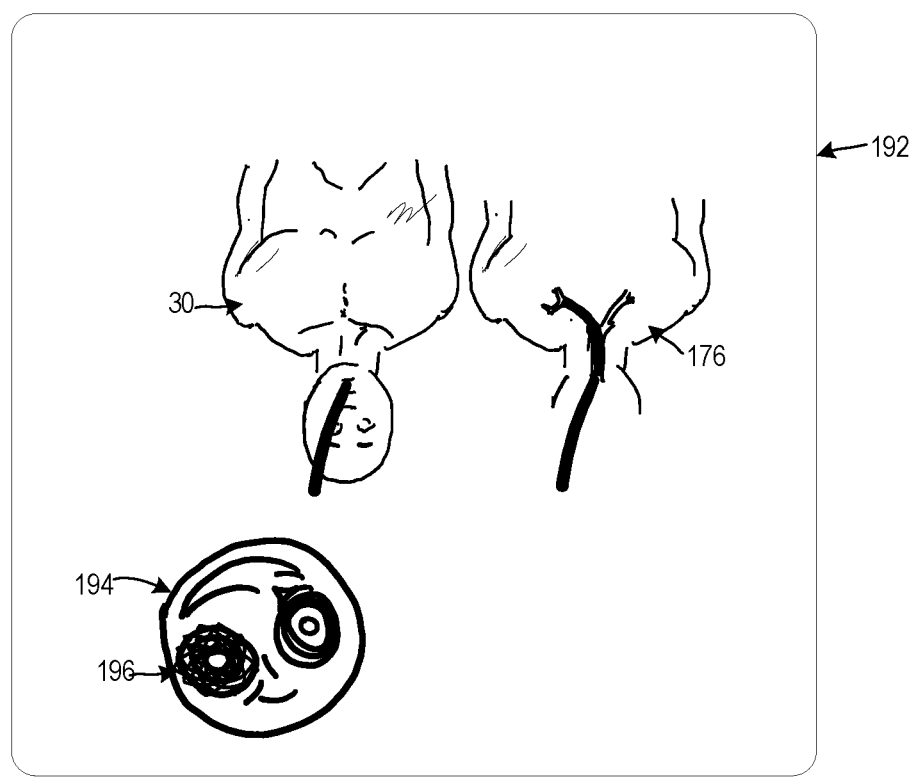
FIG. 7 is a view as seen by the viewer, according to some embodiments.

FIG. 7 illustrates a view 192 as seen by the viewer 172 in FIG. 6, according to some embodiments. The viewer 172 can see the actual body 30 of the patient and the rendering 176. The view 192 further includes a live video based on the video data that is captured by the catheter camera 82 in FIG. 4. The view 192 further shows a mesh 196 that overlays the video 194. The mesh 196 is a display of the mesh 166 in FIG. 4.

Figure 8:
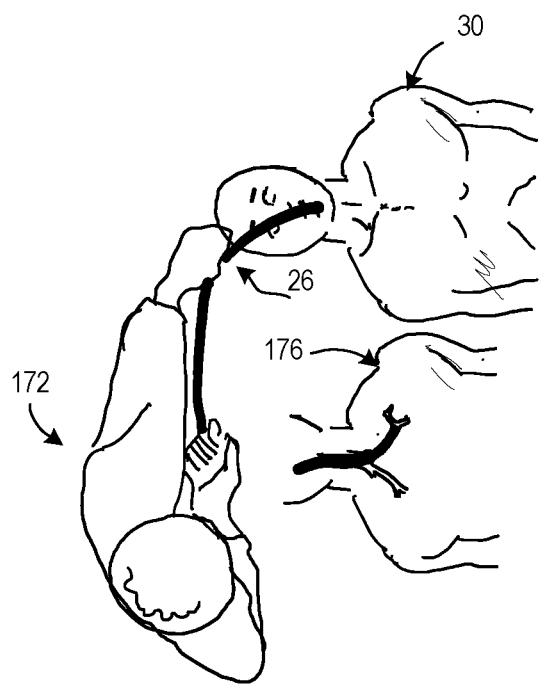
FIG. 8 is a view similar to FIG. 6 after the viewer has moved counterclockwise around the body of the patient and has moved their head counterclockwise to keep sight of the body of the patient, according to some embodiments.

In FIG. 8, the viewer 172 has moved counterclockwise around the body 30 of the patient and has also rotated their head counterclockwise to continue to see the body 30 of the patient, according to some embodiments. The display adjustment algorithm 112 detects the movement of the head of the viewer 172 and adjusts a positioning of the rendering 176 accordingly so that the rendering 176 appears to remain stationary relative to the body 30 of the patient within the view of the viewer 172.

Figure 9:
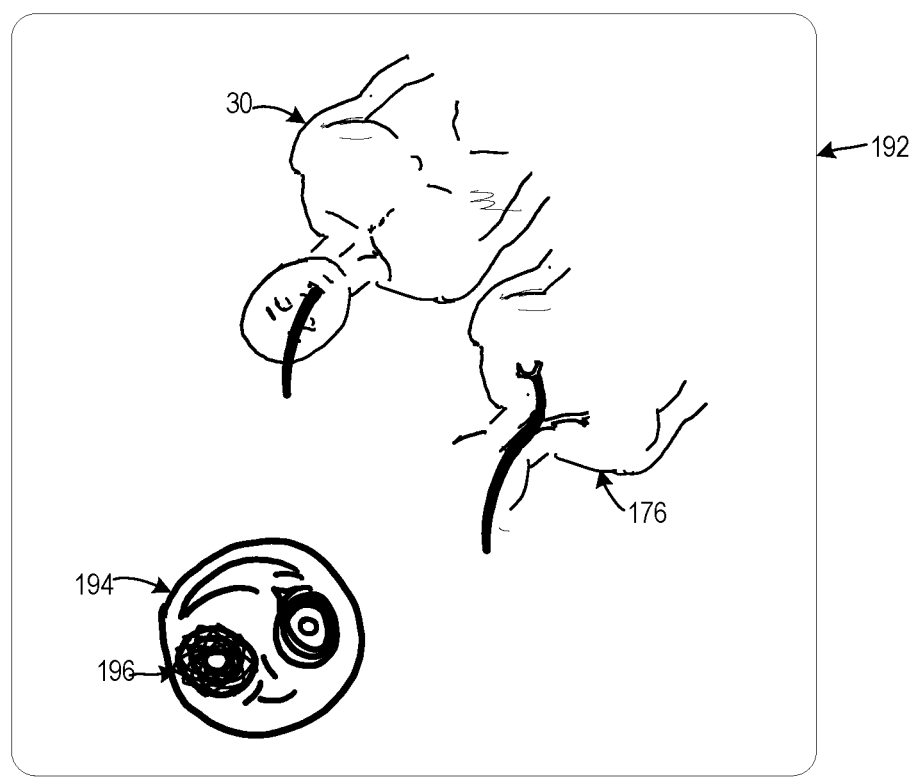
FIG. 9 is a view similar to FIG. 7 showing how the body of the patient and a rendering is modified within the view, according to some embodiments.

In FIG. 9, the body 30 of the patient has rotated clockwise relative to FIG. 7, according to some embodiments. The rendering 176 has also rotated clockwise so that it remains stationary relative to the body 30 of the patient. The location of the live video 194 has however not changed from the view 192 in FIG. 7 to the view 192 in FIG. 9. The viewer 172 thus sees the live video 194 and the mesh 196 in the same location and these components do not move upon movement of the head of the viewer 172. The viewer 172 can thus view the body 30 of the patient and the rendering 176 from different sides and angles without losing sight of the live video 194 and the mesh 196. The purpose of the mesh 196 may be to assist the viewer in guiding the tip 78 of the catheter 26 when the viewer 172 inserts the tip 78 into a passage in the body part 174 a second time after the mesh has been created, or during removal of the catheter as the catheter moves through the same path in the opposite direction. Some embodiments may have different viewing configurations for the virtual content (e.g. mesh 196, live video 194, rendering 176), in which some or all of the virtual content is fixed relative to real world coordinates, or are fixed relative to the viewer.

Figure 10:
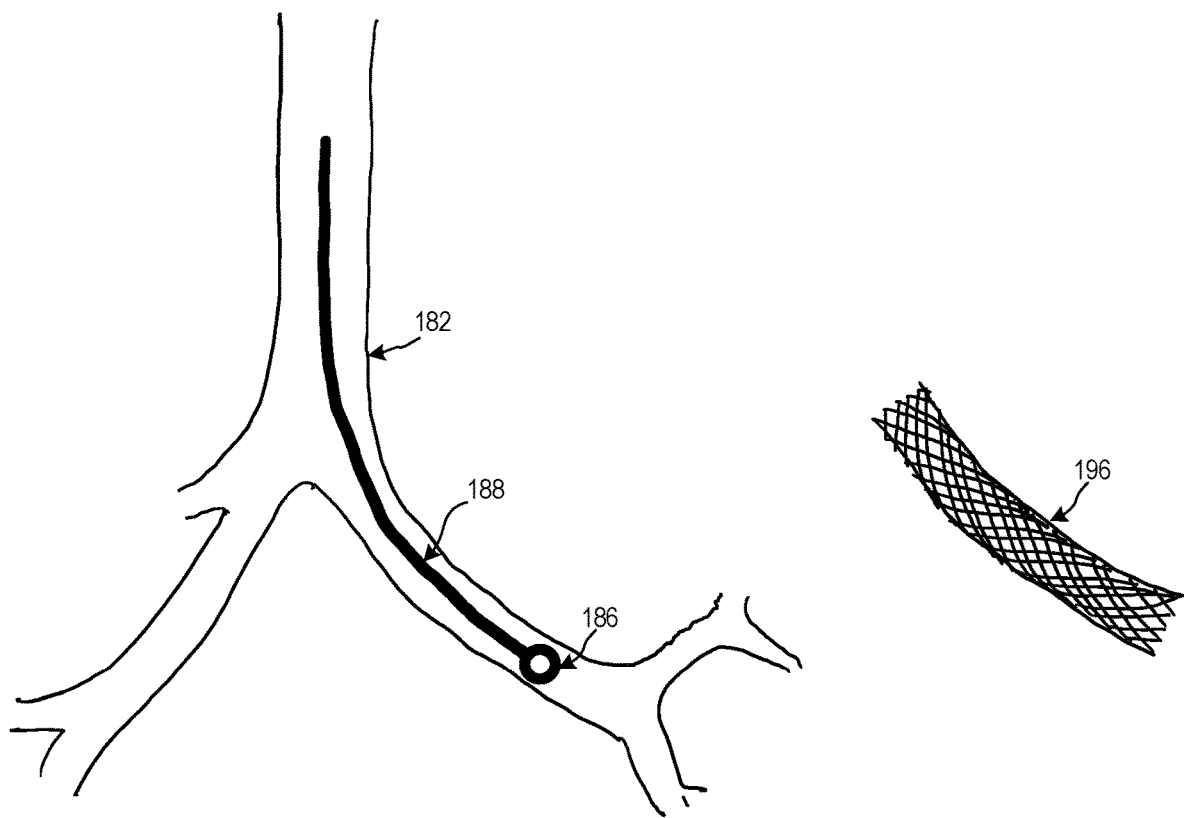
FIG. 10 illustrates renderings that are shown to the viewer in FIGS. 7 and 9 in enlarged detail, according to some embodiments.

FIG. 10 shows components of the rendering 176 that are displayed to the viewer that are too small to be seen in the views of FIGS. 7 and 9, according to some embodiments. The viewer 172 sees the renderings 182, 186 and 188 of the body part 174, the tip 78 and the past path of the tip. The viewer also sees a three-dimensional rendering of the mesh 196. The mesh 196 is shown separated from the renderings 182, 186 and 188 for purposes of illustration, although it should be understood that the mesh 196 may overlay the rendering 182 of the body part 174.

Figure 11:
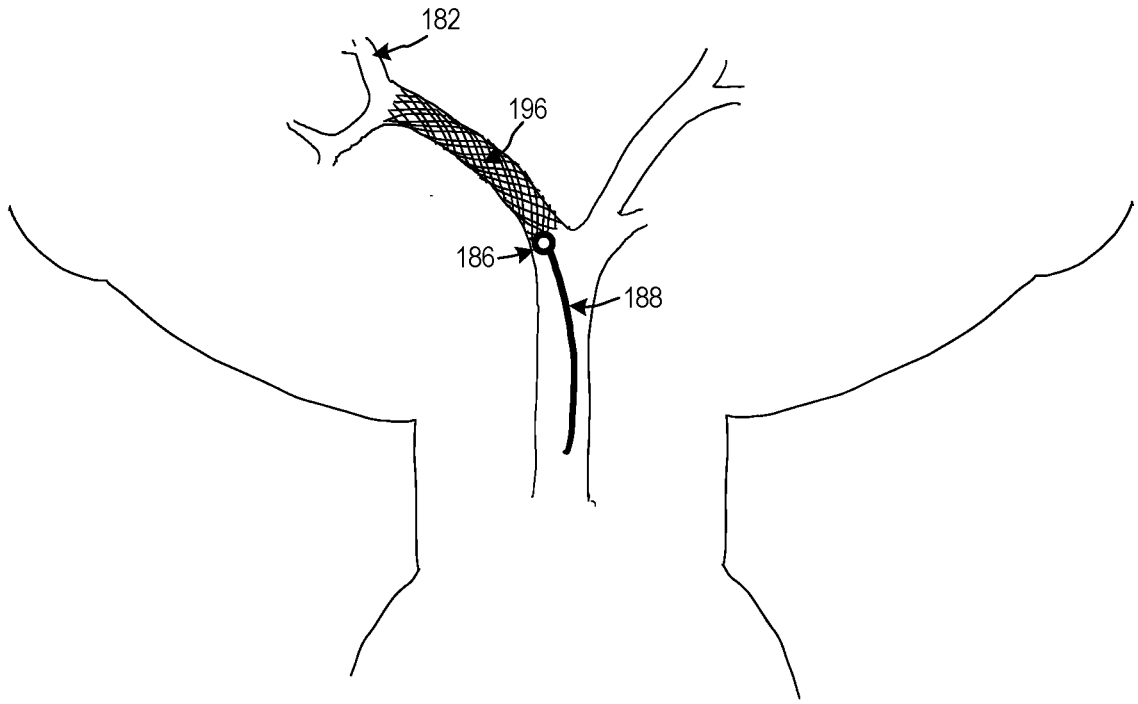
FIG. 11 is an enlarged view of a portion of a view as seen by the viewer in FIGS. 7 and 9, according to some embodiments.
Figure 12:
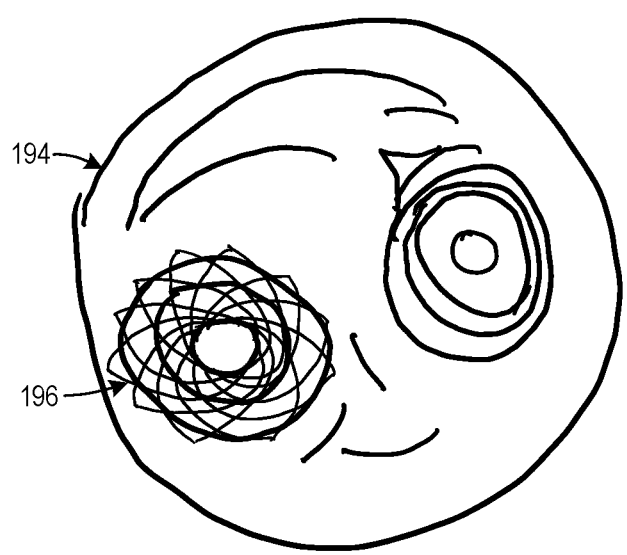
FIG. 12 is an enlarged view of live video data and a mesh as seen by the viewer in the views of FIGS. 7 and 9, according to some embodiments.

As shown in FIGS. 11 and 12, in some embodiments, the viewer 172 sees the mesh 196 in two locations, namely as part of the rendering 176 (FIG. 11) and overlaying the live video 194 (FIG. 12).

Figure 13:
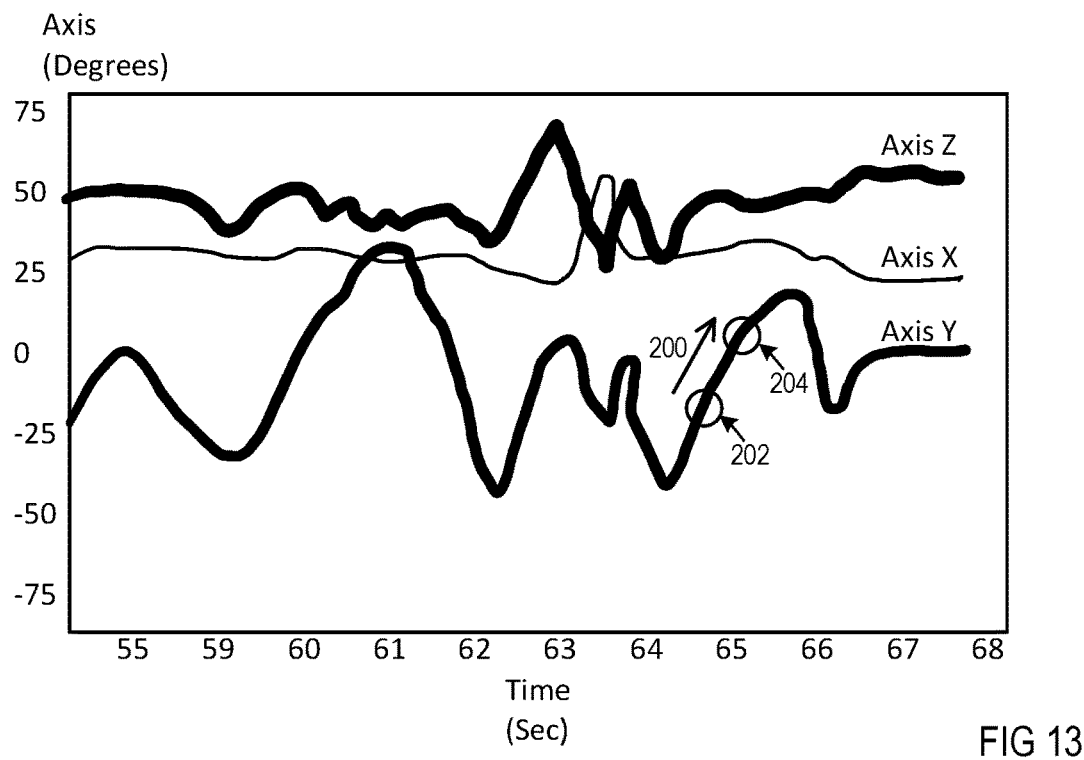
FIG. 13 is a graph illustrating three degrees of freedom of movement of the tip of the catheter and movement from a first position to a second position by a first amount, according to some embodiments.

FIG. 13 illustrates the functioning of the perspective path calculator 156 in FIG. 4, according to some embodiments. The graph illustrates rotation of the tip 78 of the catheter 26 about x- y- and x-axes over time. Rotation about each axis may be analyzed over a short amount of time to determine a first amount 200 of movement from a first position 202 to a second position 204. The first amount 200 of movement may be used to calculate a prediction of future movement of the tip 78.

Figure 14:
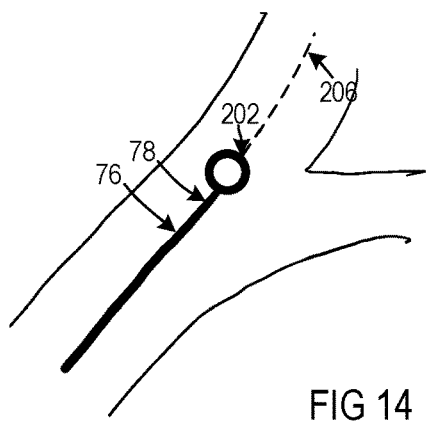
FIG. 14 is a view of the tip of the catheter in the first position, according to some embodiments.
Figure 15:
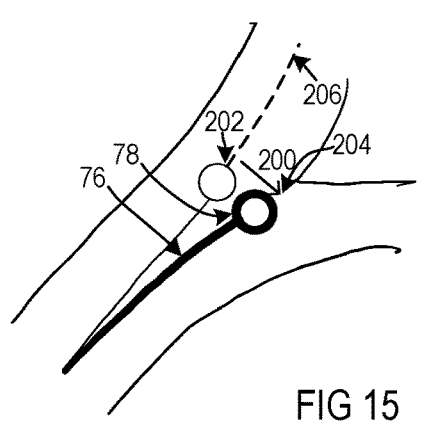
FIG. 15 is view of the catheter in the second position, according to some embodiments.

FIG. 14 illustrates the tip 78 in the first position 202, according to some embodiments. In FIG. 15, the tip 78 has moved from the first position 202 to the second position 204 by the first amount 200, according to some embodiments. The first amount 200 shown in FIG. 15 is the sumtotal of all vectors of all movements about all axes and in all translation directions.

Figure 16:
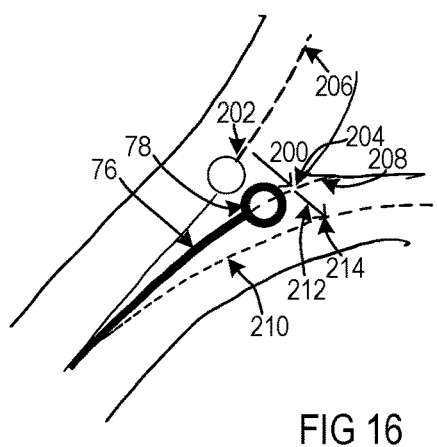
FIG. 16 is a view similar to FIG. 16 illustrating a path extending through a lumen and a path that does not extend through the lumen to avoid injury, according to some embodiments.

In FIG. 14, an assumption can be made that the direction that the tip 78 will follow, if the tip 78 is further inserted into the body part 174 is along an extension 206 of the lumen 76. FIG. 16 shows an extension 208 of the lumen 76 after the lumen 76 has moved by the first amount 200, according to some embodiments. A viewer will typically not progress the tip 78 along the path of the extension 208 because it will make contact with the body part 174 and cause injury. Instead, the viewer 172 will prefer to follow a path 210 in order to avoid injury. The path 210 is displaced by a second amount 212 from the second position 204 to a third position 214. The first amount 200 and the second amount 212 are measured in the same direction for ease of reference.

Figure 17:
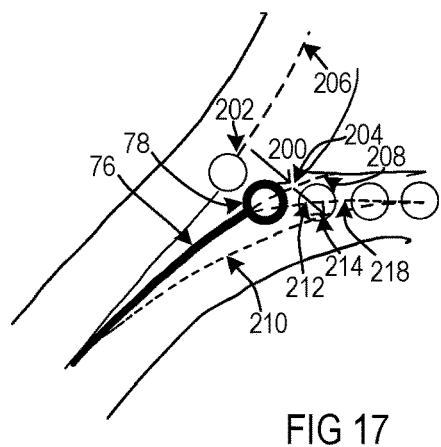
FIG. 17 is a view similar to FIG. 16 illustrating a calculated future path of the tip that is displayed as a rendering to the viewer in three-dimension, according to some embodiments.

FIG. 17 illustrates an actual path 218 that the tip 78 will likely follow, according to some embodiments. The path 218 leaves the path 208 and approaches the path 214 as the viewer inserts the tip 78 further into the body part 174. The stereoscopic analyzer 116 displays the path 218 to the viewer 172 in three-dimensions.

Figure 18:
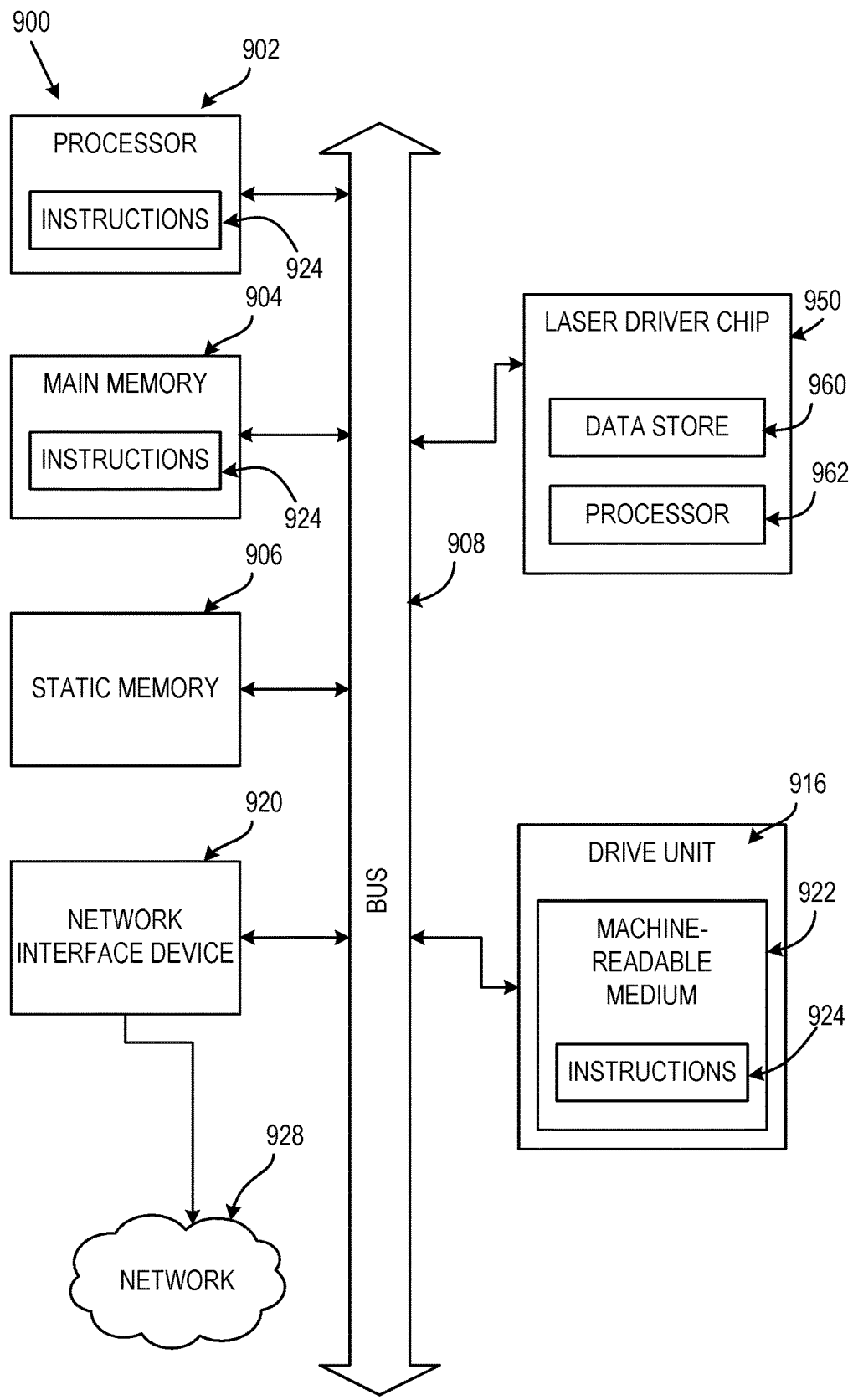
FIG. 18 is a block diagram of a machine in the form of a computer that can find application in the present invention system, in accordance with one embodiment of the invention.

FIG. 18 shows a diagrammatic representation of a machine in the exemplary form of a computer system 900 within which a set of instructions, for causing the machine to perform any one or more of the methodologies discussed herein, may be executed, according to some embodiments. In alternative embodiments, the machine operates as a standalone device or may be connected (e.g., networked) to other machines. Further, while only a single machine is illustrated, the term "machine" shall also be taken to include any collection of machines that individually or jointly execute a set (or multiple sets) of instructions to perform any one or more of the methodologies discussed herein.

The exemplary computer system 900 includes a processor 902 (e.g., a central processing unit (CPU), a graphics processing unit (GPU) or both), a main memory 904 (e.g., read only memory (ROM), flash memory, dynamic random access memory (DRAM) such as synchronous DRAM (SDRAM) or Rambus DRAM (RDRAM), etc.), and a static memory 906 (e.g., flash memory, static random access memory (SRAM), etc.), which communicate with each other via a bus 908.

The computer system 900 may further include a disk drive unit 916, and a network interface device 920.

The disk drive unit 916 includes a machine-readable medium 922 on which is stored one or more sets of instructions 924 (e.g., software) embodying any one or more of the methodologies or functions described herein. The software may also reside, completely or at least partially, within the main memory 904 and/or within the processor 902 during execution thereof by the computer system 900, the main memory 904 and the processor 902 also constituting machine-readable media.

The software may further be transmitted or received over a network 928 via the network interface device 920.

The computer system 900 includes a laser driver chip 950 that is used to drive projectors to generate laser light. The laser driver chip 950 includes its own data store and its own processor 962.

While the machine-readable medium 922 is shown in an exemplary embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

The implementation described above uses a CT scanner 22 to scan the body part 174. A CT scanner has transmitter in the form of an x-ray transmitter, a receiver in the form of an x-ray detector, and transmits and receives waves in the form of x-ray waves. It may be possible to use other scanning devices that use other transmitters and receivers and transmit and detect different waves. For example, a sonar system uses a sound transmitter to transmit a sound wave and a sound receiver to receive a sound wave. A visual system may include a light source that is inserted into the body part that transmits a light wave and have a camera that is located within the body part that captures a light wave reflected from the body part.

CT scanners are, however, preferred over other scanning devices because CT scanners provide very highly detailed raw data of the body part in three-dimensions and such data can readily be converted with an image generation unit to create three-dimensional image data. CT data also as the advantage that it can include data with respect to particular substances, materials, and densities of materials. The implementation described shows a rendering 176 placed next to the body 30 of a patient in the view 192 of the viewer 172. It may also be possible to match the rendering with the body 30 of the patient so that the rendering of the body part be where the actual body part is and the rendering of the tip of the catheter is where the actual position of the tip of the catheter is.

Aspects of the invention can also be implemented without a catheter. For example, it may be possible to scan a body of a patient to determine a growth and for a viewer to use a display system to overlay a rendering of the growth in three-dimensions on the actual body of the patient. In this manner, the viewer can "see" the growth "within' the actual body of the patient.

In certain aspects and embodiments, invasive surgical tools in general are utilized in lieu of or in addition to the described catheter. For example, with reference to FIGS. 14-17 the tip 78 may indicate the leading point of a thermal imaging camera coupled to a catheter to collect temperature data through the anatomical channel it is passing through. Thermal data may then be converted from black and white thermal images and displayed through the image reception unit 106 as a variable-color overlay to an operator. It will be appreciated that not every display need common imagery to every user. A first operator or observer (local or remote) may desire certain information display, such as temperature data indicative of arterial blood vs. venous blood or frostbite tissue, whereas a second operator or observer may desire certain information such as that indicative of position of the surgical tool. In other words, display of information need not be limited to images of a position of a tool within a patient, but may be images collected from the tool as well. In some thermal imaging embodiments, a temperature gradient can be selected per user; a first operator may want to discern organic tissue from inorganic material and set a base temperature to 98.6 degrees Fahrenheit whereas a second operator may intend to track surgical tools specifically and set a base temperature for imaging to a preset temperature rather than an absolute.

In some embodiments, operational envelopes are implemented. Returning to FIGS. 14-17, while navigating anatomical channels, a patient's particular disposition may alter the operational loads of the instrument. For example, if patient imaging indicates sensitive tissue proximate the instrument, the load may be proportionally adjusted. To further illustrate, if imaging of a patient with atrial fibrillation indicates a thin left atrial wall, an ablation catheter with a standard axial load of 0.1 N may be tented to a range of 0.01 or 0.05 N while operating in proximity to the left atrial wall. In some embodiments, the loading paradigm as a function of position, both absolute and relative to an anatomical marker such as sensitive tissue, may be displayed to operators in conjunction with instrument imagery such as position or collected images. Visual feedback may therefore be provided, indicating what the load on the instrument is capped at as function of position, to inform operators of device capabilities or limitations at that instant. Alternatively, additional operators or observers can immediately identify when an instrument is not in the correct position or exceeding patient parameters for a given procedure. Though such feedback has been described as visual, feedback may take other forms such as audio or haptic (increased resistance or friction at the instrument controls).

In some embodiments, observable motion artifacts provide positional adjustments to the instrument. Head unit cameras 102 may image patient positional data, and provide real time positional adjustment to the instrument. In some embodiments, patient breathing rhythm is observed and instrument controls are modified to accommodate for the breathing state. Head unit cameras 102 may register positional data, such as by fiducial markers within the operating environment or fixed machines of known dimensions to compare a chest position during exhale and inhale and associate changes in dimensions. In some embodiments, as the lungs expand during an inhale and surrounding anatomy compresses in reaction, instrument motion may correspondingly slow and then resume normal operational parameters as the lungs contract during exhale, or x-y-z adjustments made to match the rise and fall of the chest cavity, such that an instrument moves in absolute terms in an anatomical channel but is stable relative to that anatomical reference. Other observed triggers may provide operational adjustments as well, and heart rate and expected contraction/dilation of blood vessels may provide positional updates to the instrument.

In some embodiments, the feedback control of patient activity (e.g., breathing rhythm, heartbeat) is collected at three separate times by head unit cameras 102 at times $T_1$ to $T_2$ to $T_3$, and the images are analyzed at time $T_4$ to determine a change in patient position (due to movement of the patient, their breathing rhythm, heartbeat, etc.). An instrument operatively coupled to head unit camera 102 is given a control input at time $T_0$ (i.e. before or concurrent with $T_1$), and an adjustment to the control input based on the change in patient position observed over the times $T_1$ to $T_3$ is made at time $T_5$. In some embodiments, the change in control input is a fraction of the measured change in patient position.

Figure 19:
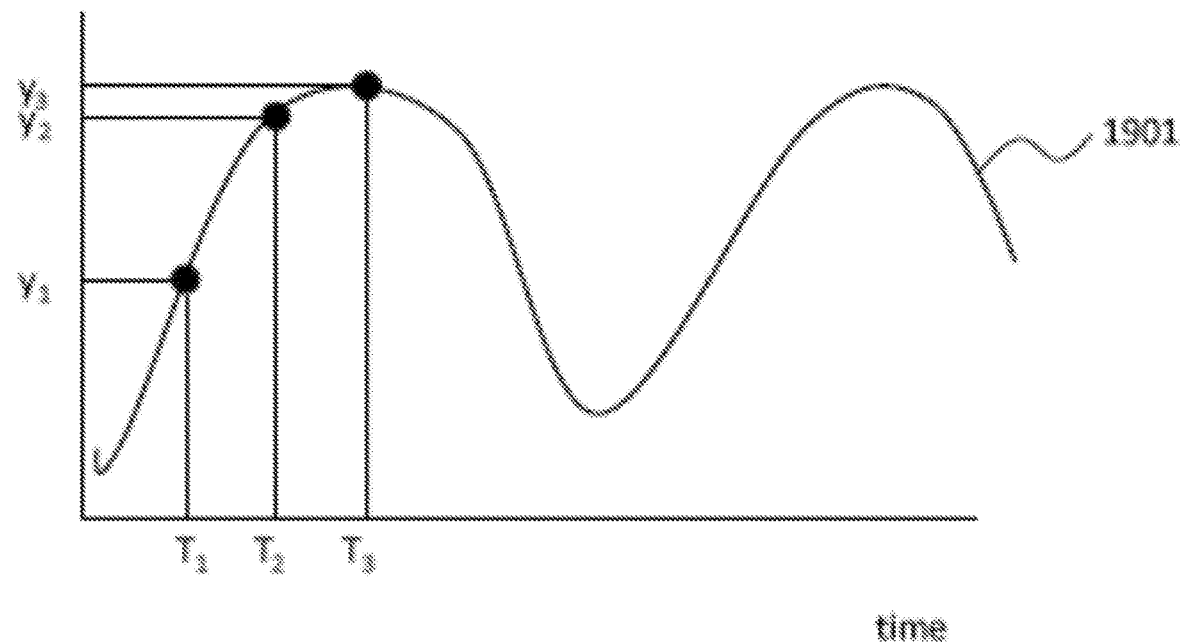
FIG. 19 illustrates a timing relationship for adjusting medical instrument inputs as a function of patient observed position changes, in accordance with one embodiment of the invention.

FIG. 19 illustrates an exemplary relationship between measured patient position data and control feedback adjustments. As depicted, a theoretical y direction change in patient position by chest expansion incident to breathing is represented by curve 1901. Observed patient position data is collected at times $T_1$, $T_2$, and $T_3$, corresponding to chest position $y_1$, $y_2$, and $y_3$ respectively. Preferably, three collection times are made to provide trends analysis for the target measurement. For example, the average human breathing rate is 15 breaths per minute, allocating approximately 2 seconds for any given inhale or exhale. To avoid corrections to instrument positions that are based on measured inhales but are applied during exhales, at least three measurements are taken to provide trend analysis. Given average human breathing rate, a time interval between measurements of at least 0.667 second or 1.5 Hz is preferred. Such frequency need not be the time between each of $T_0$ and $T_5$, and it is preferable to have the associated actions at $T_4$ and $T_5$ applied as quickly as possible.

Returning to FIG. 19, the change in position $y_1$ to $y_2$ to $y_3$ indicates to the system during analysis at $T_4$ that an inhale is concluding proximate to $T_3$. As such, the feedback control at $T_5$ may provide no adjustment, to avoid applying an "inhale correction" during an exhale, or may provide a negative y position adjustment based on the time relation of $T_5$ to $T_3$ and extrapolated y position change. For example, if the time between $T_3$ and $T_5$ is similar to the time between $T_2$ and $T_3$, and the system recognizes from the change as between $y_1$ and $y_2$ as compared to $y_2$ and $y_3$ that the patient is experiencing a change in y direction, then the adjustment may be less than or equal to the change as measured from $T_2$ to $T_3$. This may be depicted as logic relationship below:

$$\text{IF}(T_5-T_3=T_3-T_2)\cap(y_3-y_2)<(y_2-y_1), \text{ then correction at } T_5<(y_3-y_2).$$

While certain exemplary embodiments have been described and shown in the accompanying drawings, it is to be understood that such embodiments are merely illustrative and not restrictive of the current invention, and that this invention is not restricted to the specific constructions and arrangements shown and described since modifications may occur to those ordinarily skilled in the art.

What is claimed:
1. A patient viewing system comprising;
a catheter having a lumen and a tip;
a tip tracking device that detects movement of the tip;
left and right projectors;

left and right light wave guides connected to the left and right projectors;
a processor;
a computer-readable medium connected to the processor;
a data store on the computer-readable medium;
image data stored on the data store;
a set of instructions stored on the computer-readable medium and executable by the processor, including:
a catheter tracking system that is connected to the tip tracking device, wherein the catheter tracking system receives a measurement based on movement detected by the tip tracking device, determines a position of the tip based on the measurement, and stores the position of the tip in the data store; and
a stereoscopic analyzer connected to the data store to receive the image data, the stereoscopic analyzer determining left and right image data sets, the left and right projectors projecting the left and right image data sets respectively, the left and right image data sets differing from one another to give the viewer a perception of a three-dimensional rendering.

2. The patient viewing system of claim 1, further comprising:
a head-mountable frame, the light wave guides being secured to the head-mountable frame.

3. The patient viewing system of claim 2, wherein the light wave guides are transparent light wave guides positioned between the eyes and the external surface of the body.

4. The patient viewing system of claim 2, further comprising:
a head unit detection device that detects movement of the head-mountable frame,
the set of instructions including:
a display adjustment algorithm that is connected to the head unit detection device and receives a measurement based on movement detected by the head unit detection device and calculates placement value; and
a display positioning algorithm that modifies a position of the body part within a view of the eye based on the placement value.

5. The patient viewing system of claim 4, wherein the head unit detection device includes:
a head unit inertial measurement unit (IMU) mounted to the head-mountable frame, the head unit IMU including a motion sensor that detects movement of the head-mountable frame.

6. The patient viewing system of claim 4, wherein the head unit detection device includes:
a head unit camera mounted to the head-mountable frame, the head unit camera detecting movement of the head-mountable frame by taking images of objects within view of the head unit camera.

7. The patient viewing system of claim 6, the set of instructions including:
an image processing system that analyzes the images to detect a pose position of the head-mountable frame.

8. The patient viewing system of claim 1, further comprising:
a transmitter;
an energy source connected to the transmitter to activate the transmitter, a body of a patient being positionable relative to the transmitter for the transmitter to generate a forward wave at a body part within the body;
a receiver positionable relative to the body to detect a return wave from the body part, the return wave from the body part being in response to the forward wave created by the transmitter,
the set of instructions including:
a raw data reception unit that receives raw data of the return wave detected by the receiver and stores the raw data in the data store;
an image generation unit connected to the data store to process the raw data of the return wave to create image data representing an image and store the image data in the data store;
an image data reception unit that receives the image data from the data store; and
a catheter display integrator that combines the position of the tip with the image data, the pattern of light created by the projector including the pattern representative of the image data and the position of the tip.

9. The patient viewing system of claim 8, comprising:
a computed tomography (CT) scanner including:
a base;
a platform for the patient; and
a rotor mounted to the base for rotation about the patient, wherein the transmitter is an x-ray transmitter secured to the rotor and transmitting an x-ray wave and the receiver is an x-ray detector secured to the rotor to detect the x-ray wave, movement of the platform relative to the base allowing for movement of the patient relative to a plane extending from the x-ray transmitter to the x-ray detector.

10. The patient viewing system of claim 1, the set of instructions including:
a past path calculator that stores a past path of the tip in the data store, the catheter display integrator displaying the past path of the tip together with position of the tip.

11. The patient viewing system of claim 1, the set of instructions including:
a past path calculator that stores a past path of the tip; and
a mesh generator that generates a three-dimensional mesh around the past path of the tip and stores the mesh in the data store, the catheter display integrator displaying the mesh together with position of the tip.

12. The patient viewing system of claim 11, further comprising:
a catheter camera in the tip, the catheter camera capturing video data,
the set of instructions including:
a video data reception unit connected to the catheter camera in the tip to receive the video data, the catheter display integrator displaying a live video based on the video data.

13. The patient viewing system of claim 1, the set of instructions including:
a prospective path calculator that calculates a future path of the tip based the position of the tip, the catheter display integrator displaying the future path.

14. The patient viewing system of claim 13, wherein the future path is calculated based on the movement detected by the tip tracking device.

15. The patient viewing system of claim 14, wherein the movement detected by the tip tracking device is a first amount of movement from a first position to a second position though a first angle in a selected direction and the future path is a second amount of movement from the second position to a third position through a second angle in the selected direction.

16. The patient viewing system of claim 1, further comprising:
an invasive surgical tool on the tip.

17. The patient viewing system of claim 1, further comprising:
a camera on the tip; and
at least one display to display images captures by the camera to an operator.

18. The patient viewing system of claim 17, wherein a first display displays the three-dimensional rendering and the images captured by the camera to a first operator.

19. The patient viewing system of claim 17, wherein a first display displays the three-dimensional rendering to a first operator, further comprising:
a second display that displays the images captured by the camera to a second operator.

20. The patient viewing system of claim 1, further comprising:
a first display to display the three-dimensional rendering to a first operator;
a data collection system collecting data without the catheter; and
a second display to display the data collected with the data collection system to a second operator.

21. The patient viewing system of claim 1, further comprising:
a load detection system connected to the tip to determine operational load on the tip; and
a warning system connected to the load detection system to warn an operator if a load on the tip exceeds a predetermined limit.

22. The patient viewing system of claim 21, wherein the warning is one of a visual warning, an audio warning and a haptic warning.

23. The patient viewing system of claim 1, further comprising:
a motion detection system to observe motion artifacts; and
a positional adjustment system connected to the motion detection system to make positional adjustments to the tip based on the motion artifacts.

24. The patient viewing system of claim 23, wherein the motion detection system collects feedback control images of patient activity at three separate times at times T1 to T2 to T3, and the images are analyzed at time T4 to determine a change in patient position and an adjustment to the control input based on the change in patient position observed over the times T1 to T3 is made at time T5.

* * * * *